(12) United States Patent
Masuda

(10) Patent No.: US 7,282,036 B2
(45) Date of Patent: Oct. 16, 2007

(54) COSMETIC DEVICE HAVING VIBRATOR

(76) Inventor: Masatoshi Masuda, 2, 9-banchi, Takada-Cho, Saiin, Ukyo-ku, Kyoto-city, Kyoto, 615-0031 (JP)

( * ) Notice: Subject to any disclaimer, the term of this patent is extended or adjusted under 35 U.S.C. 154(b) by 388 days.

(21) Appl. No.: 10/970,614

(22) Filed: Oct. 20, 2004

(65) Prior Publication Data
US 2005/0113725 A1 May 26, 2005

(30) Foreign Application Priority Data
Oct. 24, 2003 (JP) ............................. 2003-364672
May 18, 2004 (JP) ............................. 2004-147881

(51) Int. Cl.
*A61H 23/02* (2006.01)
(52) U.S. Cl. ...................... 601/72; 601/2; 601/70; 601/138
(58) Field of Classification Search ............ 601/2, 601/15, 17, 18, 46, 67, 69, 70, 72, 73, 80, 601/82, 138, 89, 93, 94, 95; D24/211, 214
See application file for complete search history.

(56) References Cited
U.S. PATENT DOCUMENTS
3,585,990 A * 6/1971 Blachly et al. ............... 601/72
5,336,159 A * 8/1994 Cheng ........................ 601/15
6,170,108 B1 * 1/2001 Knight ........................ 601/17
2004/0068213 A1 * 4/2004 Fujisawa ..................... 601/70

FOREIGN PATENT DOCUMENTS
DE 94 09 230 U 7/1994
JP 2003-116951 4/2003

* cited by examiner

*Primary Examiner*—Quang D. Thanh
(74) *Attorney, Agent, or Firm*—Knobbe, Martens, Olson & Bear LLP

(57) ABSTRACT

A cosmetic device comprises a support member; a cap member attached to the support member and having a front face; a vibration actuator disposed inside the cap member, which produces vibration for providing massage effect on a skin; and an uneven surface member as an outermost layer covering at least the front face of the cap member. The uneven surface is configured to prevent denudation of a treatment agent applied on the skin.

32 Claims, 28 Drawing Sheets

COSMETIC DEVICE HAVING VIBRATOR

BACKGROUND OF THE INVENTION

1. Field of the Invention

The present invention generally relates to a cosmetic device which produces a beauty effect by applying vibration to the skin.

2. Description of the Related Art

As such cosmetic devices, for example, a cosmetic device described in Japanese Patent Laid-open No. 2003-205008 is known. The cosmetic device described in the Patent reference comprises a device main unit incorporating a vibration-producing means. A tip used for beauty treatment comprising a porous member is fixed in the fore-end of the device main unit; by contacting this tip for beauty treatment with a skin surface, vibration of the device main unit is transmitted to the skin.

According to the cosmetic device described in the Patent reference, because the tip for beauty treatment comprises the porous member, a beauty treatment agent can be impregnated and kept inside the porous member. By this, massage effect on the skin can be produced, thereby enabling uniformly exfoliating of dead skin cells.

In order to maintain beauty effects from the beauty treatment agent having been applied onto the skin surface, it is required that the beauty treatment agent be applied onto the skin surface uniformly without denudation. If the tip for beauty treatment, which contacts the skin surface, has a sharp plane angle in its contact surface, the beauty treatment agent which has been applied onto the skin surface is denuded by the sharp angle, making it difficult to apply the beauty treatment agent onto the skin surface uniformly.

Given this factor, it is desirable to form a plane angle in the skin-contact surface of the beauty treatment tip, which contacts the skin surface, into a rounded shape.

The tip for beauty treatment in the cosmetic device described in the Patent reference, however, has a problem in that a sophisticated processing technique is required to form a rounded plan angle in the skin-contact surface of the tip for beauty treatment. Additionally, producing such beauty treatment tips is expensive.

Furthermore, the cosmetic device described in the Patent reference, from the viewpoint of its configuration, it is difficult to dispose the beauty treatment tip and the vibration-producing means adjacently. For this reason, vibration produced by the vibration-producing means cannot be transmitted effectively to the tip for beauty treatment; and hence massage effect on the skin cannot be produced effectively.

As other cosmetic devices, a cosmetic device described in Japanese Patent Laid-open No. 2001-190586 is known. The cosmetic device described in the Patent reference comprises a probe which can be contacted with the skin of a person receiving a treatment and a vibration-producing means vibrating the probe. This device further comprises a Peltier element which is disposed adjacently to the probe. Consequently, the device described in the Patent Reference enables to give vibration to the skin of a person receiving a treatment as well as to heat and cool the skin of the person receiving a treatment alternately.

In the case of the cosmetic device described in the Patent reference, however, vibration produced by the vibration-producing means is transmitted not only to the probe but also to a main unit supporting the probe. Consequently, there is a problem in that an operator operating other parts disposed in the main unit and the main unit is adversely affected.

SUMMARY OF THE INVENTION

The present invention has been achieved to solve one or more of the above-mentioned problems or related problems. In an aspect, an object of the present invention is to provide a cosmetic device which can produce massage effect on the skin while processing the device is easy and at low cost as well as denudation of the beauty treatment agent having been applied onto the skin can be prevented effectively. In an aspect, an object of the present invention is to provide a cosmetic device capable of preventing vibration produced by the vibration-producing means from being transmitting to the main unit.

The present invention can accomplish one or more of the above-mentioned objects in various embodiments. The present invention is not intended to be limited by the above objects, and various objects other than the above can be accomplished as readily understood by one of ordinary skill in the art. The embodiments described below use reference numbers used in the drawings solely for easy understanding, and the reference numbers are not intended to limit the scope of the invention.

In an aspect, the present invention is to provides a cosmetic device comprising: (i) a support member (e.g., 10, 110); (ii) a cap member (e.g., 20, 120) attached to the support member and having a front face (e.g., 21, 121); (iii) a vibration actuator (e.g., 40, 140), disposed inside the cap member, which produces vibration for providing massage effect on a skin; and (iv) an uneven surface member (e.g., 30, 130, 230) as an outermost layer covering at least the front face of the cap member, said uneven surface being configured to prevent denudation of a treatment agent applied on the skin.

The above embodiment includes, but is not limited to, the following embodiments:

The uneven surface member may be a porous member. The porous member may be a resilient sponge material. The uneven surface member may be replaceable.

The cosmetic device may further comprise a ring member (e.g., 50, 150, 250) for fixing the uneven surface member wherein the uneven surface member is fixed between the ring member and the cap member. The ring member may have an inner circumference having an annular concave (e.g., 55, 152, 252), and the cap member may have an outer circumference having an annular convex (e.g., 25, 125), wherein the uneven surface member is fixed between the annular concave of the ring member and the annular convex of the cap member. The ring member may have an outer circumference having multiple nail portions (e.g., 51) which are engaged with the support member.

The cap member may have an annular flange (e.g., 26, 126), which is engaged with the support member. The cap member may have an inner surface provided with a supporting structure (e.g., 41, 124) to which the vibration actuator is supported.

The front face of the cap member may have a rounded annular edge (e.g., 23).

The uneven surface member may be preformed in a shape corresponding to a shape of the cap member. The uneven surface member may be made of a planate material having flexibility and is shaped when is fixed to the cap member with the ring member.

The support member may have a gripper (e.g., 100, 200). The vibration actuator is battery-operated. The support member may be configured to accommodate a battery or batteries.

The front face of the cap member may comprise at least one annular pleat structure (e.g., 122) substantially or nearly concentric with an outer circumference (e.g., 123). The at least one annular pleat structure may be constituted by multiple pleat portions. The vibration actuator may be provided substantially or nearly in a center of the front face of the cap member.

The cosmetic device may further comprise a conductive cap member (e.g., 160) attached to the support member, said conductive cap member having a front face (e.g., 161), wherein an ultrasonic oscillator (e.g., 170) is attached to an inner wall of the front face. The support member may be configured to be connected to an external ultrasonic signal generator (e.g., 301). The conductive cap member may be electrically connected to an external low frequency current generator (e.g., 302) and/or an external moderate frequency current generator (e.g., 305). The support member may be provided with a ground terminal (e.g., 220, 240) which is in contact with a user's hand when in use.

The uneven surface member may be constituted by multiple fine protrusions (e.g., 330). The front face of the uneven surface member may be curved in a partial sphere. The multiple fine protrusions may be formed in circles concentric with each other.

In another aspect, the present invention is to provide a cosmetic device comprising: (i) a support member (e.g., 10, 110); (ii) a cap member (e.g., 20, 120) attached to the support member and having a front face (e.g., 21, 121); (iii) a vibration actuator (e.g., 40, 140) disposed inside the cap member, which produces vibration for providing massage effect on a skin; (iv) a replaceable uneven surface member (e.g., 30, 130, 330) as an outermost layer covering at least the front face of the cap member, said uneven surface being such that denudation of a treatment agent applied on the skin is inhibited; and (v) a ring member (e.g., 50, 150, 250) to fix the uneven surface member wherein the uneven surface member is fixed between the ring member and the cap member.

The above embodiment includes, but is not limited to, the following embodiments:

The uneven surface member may be constituted by a porous member (e.g., 30, 130) or multiple fine protrusions (e.g., 330). The front face of the cap member may comprise at least one annular pleat structure (e.g., 122) substantially or nearly concentric with an outer circumference.

In still another aspect, the present invention is to provide a cosmetic device comprising: (i) a support member (e.g., 10, 110); (ii) a first cap member (e.g., 20, 120) attached to the support member and having a front face (e.g., 21, 121); (iii) a vibration actuator (e.g., 40, 140) disposed inside the cap member, which produces vibration for providing massage effect on a skin; (iv) an uneven surface member (e.g., 30, 130, 330) as an outermost layer covering at least the front face of the cap member, said uneven surface being such that denudation of a treatment agent applied on the skin is inhibited; and (v) a second cap member (e.g., 160) attached to the support member, wherein an ultrasonic oscillator (e.g., 170) is provided inside the second cap member.

The above embodiment includes, but is not limited to, the following embodiments:

The uneven surface member may be constituted by a porous member (e.g., 30, 130) or multiple fine protrusions (e.g., 330). The front face of the first cap member may comprise at least one annular pleat structure (e.g., 122) substantially or nearly concentric with an outer circumference. The second cap member may be made of titanium or a titanium alloy. The second cap member may be connected to an external low frequency current generator (e.g., 302) and/or an external moderate frequency current generator (e.g., 305).

In all of the aforesaid embodiments, any element used in an embodiment can interchangeably be used in another embodiment unless such a replacement is not feasible or causes adverse effect.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention. The drawings are overly simplified for illustrative purposes.

Explanation of symbols used is as follows: 10: Support member; 11: Opening portion; 11a: Convex portion; 12: Support member; 13: Opening portion; 13a: Convex portion; 14: Indicators/buttons; 15: Fingers; 20: Cap member; 21: Front face; 22: Female screw portion; 23: Corner portion; 25: Annular convex; 26: Flange; 30: Sponge member; 40: Vibration motor; 41: Motor fixing member; 42: Male screw; 50: Fixing member; 51: Nail portion; 51a: Concave portion; 55: Annular concave; 100: Gripper; 110: Support member; 120: First cap member; 121: Front face; 122: Pleat portion; 122a: Lower portion; 122b: Higher portion; 123: Outer circumference portion; 120: Support portion; 125: Annular convex; 126: Flange; 130: Sponge member; 140: Vibration motor; 141: Main unit; 142: Weight; 143: Revolving shaft; 150: Fixing member; 160: Second cap member; 161: Front Face; 170: Ultrasonic oscillator; 180: Operating panel; 181: Distribution board; 191: Inner mold; 192: Outer mold; 200: Gripper; 201: Lid; 210: Cord connection; 220: Ground terminal; 222: Pleat portion; 230: Uneven surface member; 240: Ground terminal; 250: Fixing member; 252: Annular concave; 253: Flange; 301: Ultrasonic signal generator; 302: Low frequency current generator; 303: Controller; 304: Input unit; 305: Moderate frequency current generator; 330: Multiple fine protrusions.

DETAILED DESCRIPTION OF THE PREFERRED EMBODIMENT

The present invention will be explained with respect to preferred embodiments. However, the present invention is not limited to the preferred embodiments. The preferred embodiments of the present invention are described below by referring to drawings attached.

Figure 1:
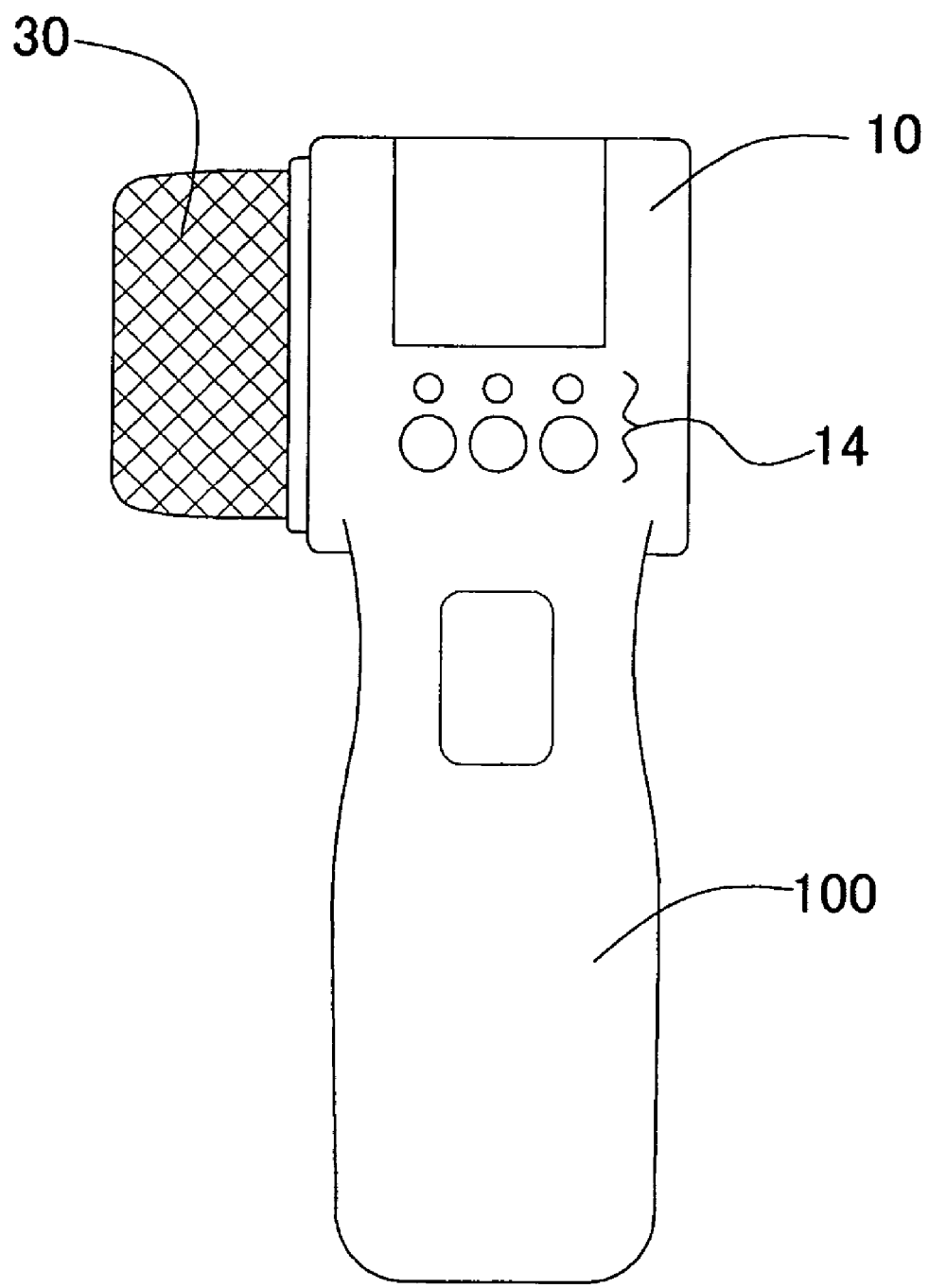
FIG. 1 is a front view showing the cosmetic device according to an embodiment of the present invention.
Figure 2:
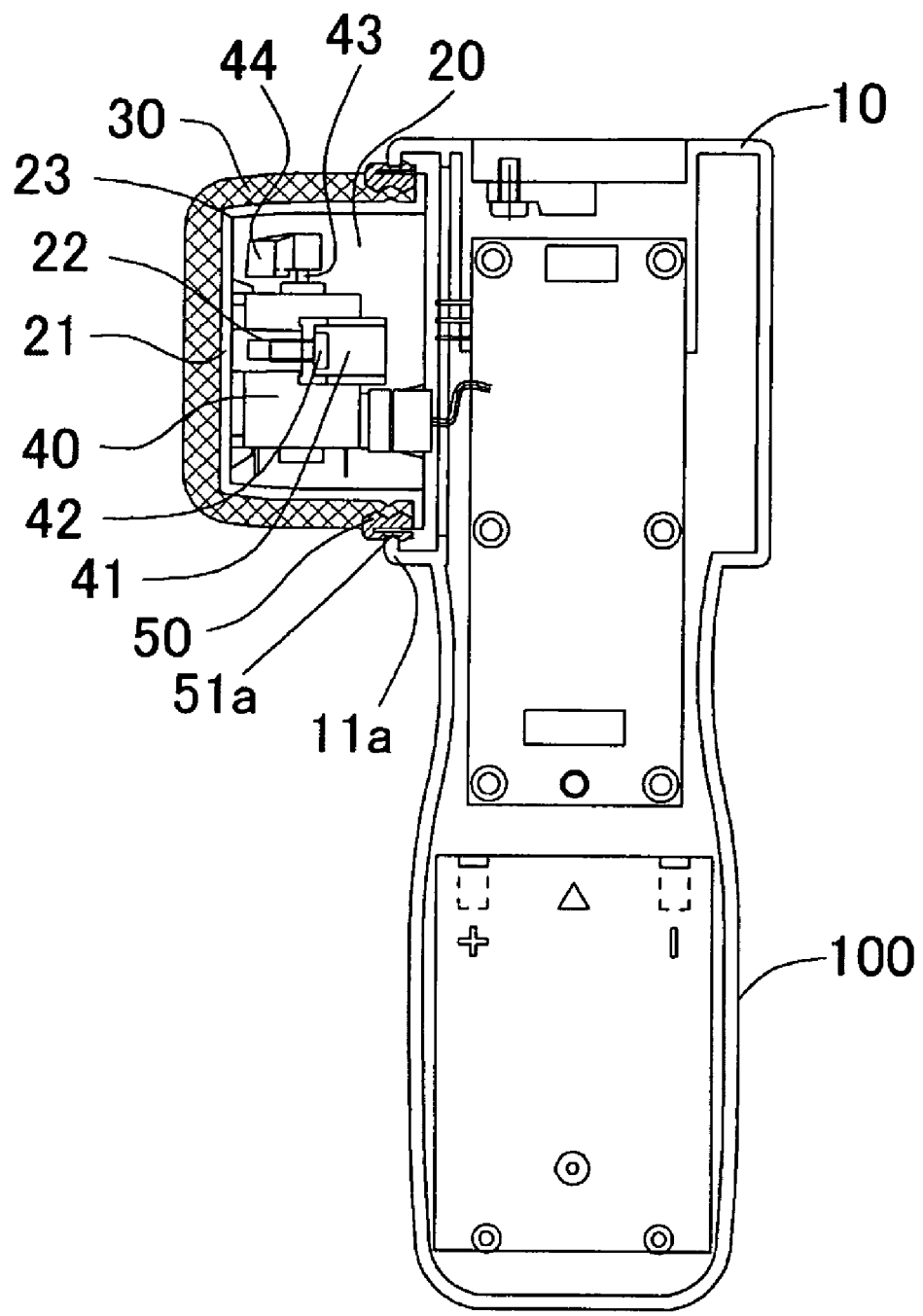
FIG. 2 is a cross section showing the cosmetic device according to an embodiment of the present invention.
Figure 3:
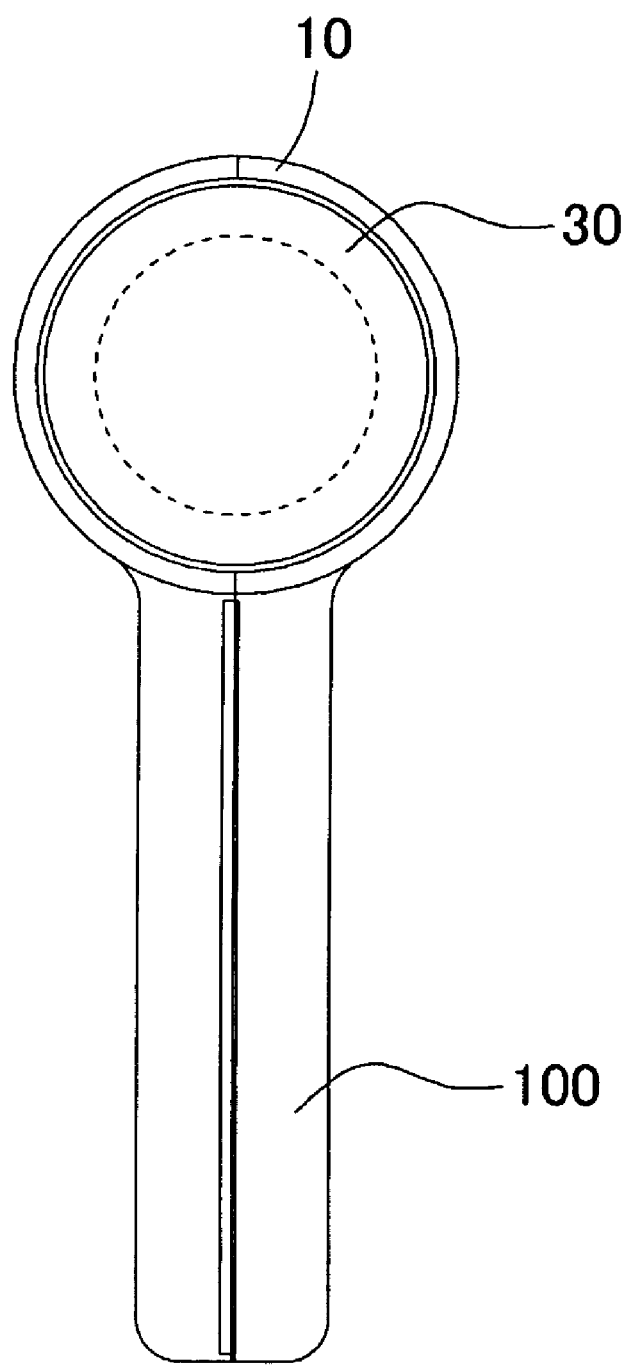
FIG. 3 is a lateral view of FIG. 1 seen from the left side.

FIG. 1 is a front view showing the cosmetic device according to an embodiment of the present invention. FIG. 2 is a cross section of FIG. 1. FIG. 3 is a left lateral view of FIG. 1.

The cosmetic device according to an embodiment of the present invention comprises a support member 10, a cap member 20 disposed in the upper portion of the support member 10, a sponge member 30 as a porous member covering outer circumference of the cap member 20, a fixing member 50 for fixing the cap member 20 and the sponge member 30, and a vibration motor 40 as a vibration actuator producing vibration. The support member 10 includes a griper 100 and multiple indicators and buttons 14.

In this specification, the vibration motor can be any motor producing vibration including those having an eccentric rotor.

The cap member 20 has a cylindrical shape having a bottom. The cap member 20 is constituted by a convex portion having a front face 21. The peripheral surface of the cap member 20 projects from a surface of the support member 10 when fixed with the support member 10.

The sponge member 30 has a shape covering at least the front face 21 of the cap member 20. Areas in this sponge member, which correspond to corner portions 23 of the cap member 20, have a curved shape.

In this embodiment, the sponge member 30 is a porous member used as an uneven surface member. Any porous material having flexibility including porous resins (such as polyethylene based resins), porous rubber, porous ceramics can be used. Preferably, porous materials such as those used for power foundation or two-way foundation, which have resistance to oil, light, and discoloration, may be used. One example is rubber (acrylonitril-butadiene rubber) which can produce a soft sponge. The thickness of the sponge member may be about 3 mm to about 30 mm (preferably, about 5 mm to about 20 mm) in the absence of pressure or tension. When the sponge member is fixed to the cap member, the thickness may be reduced by about 5% to about 80%.

The cap member may be made of a resin such as polyethylene or polypropylene or a mixture of polyethylene/polypropylene with a rubber material.

Figure 4:
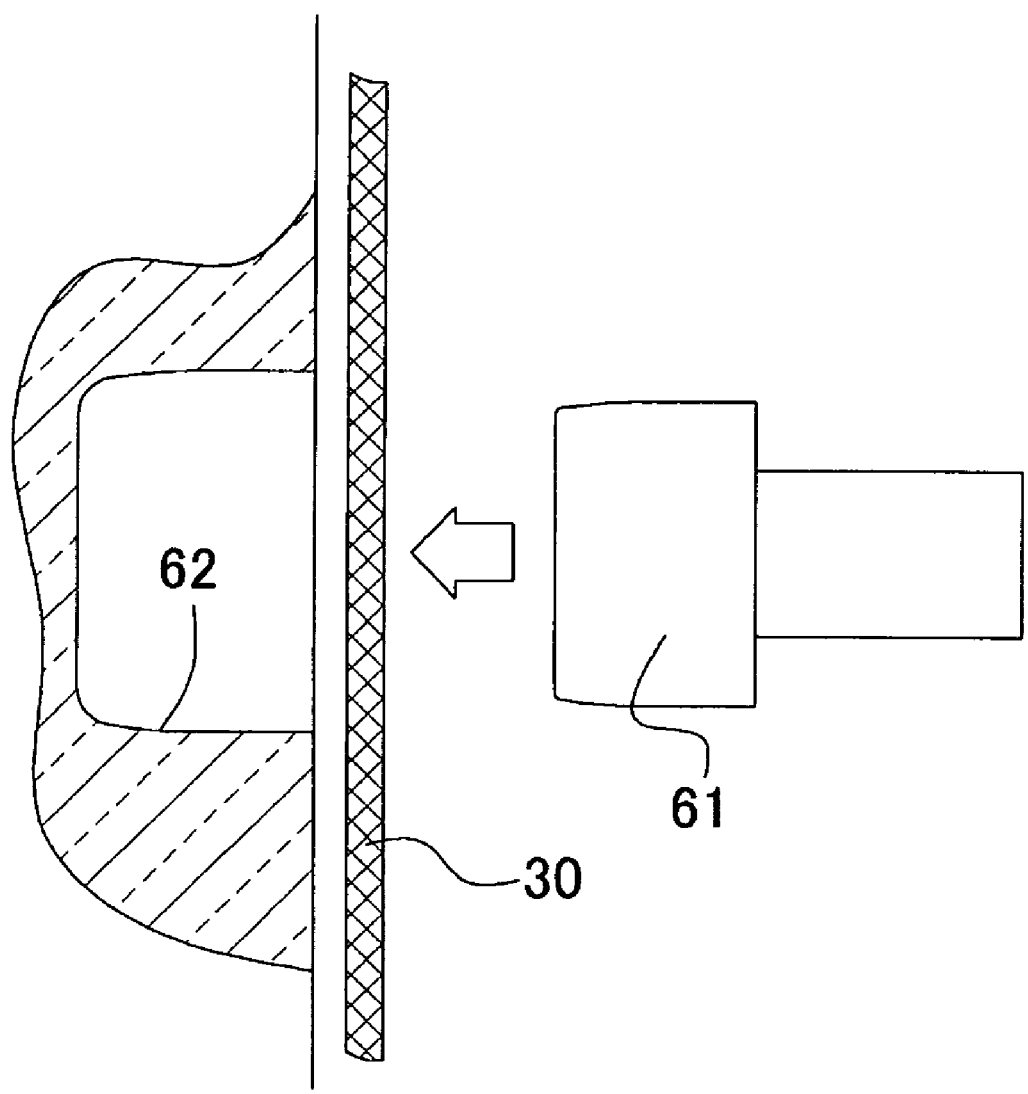
FIG. 4 is an explanatory diagram showing how the sponge member 30 is formed into a shape.

FIG. 4 is an explanatory diagram showing how the sponge member 30 is formed into a shape.

A planate sponge member 30 is inserted between an inner mold 61 shaping a contact surface of the sponge member 30, which contacts with the cap member 20, and an outer mold 62 shaping an outer surface of the sponge member 30; and then, the inner mold 61 moves in an arrow direction (in a direction of the outer mold 62) with pressing force sufficiently for deforming the sponge member 30. By this, the contact surface of the sponge member 30, which contacts with the cap member 20, is deformed to the same shape as that of the inner mold 61, and the outer surface of the sponge member 30 is deformed to the same shape as that of the outer mold 62. At this time, the inner mold 61 has nearly the same shape as a shape of the front face 21 of the cap member 20; the corner portions 23 of the outer mold 62 should have a rounded shape. Therefore, the sponge member 30 shaped by these inner mold 61 and outer mold 62 is formed into a shape accommodating a shape of the front face 21 of the cap member 20, and at the same time, its outer surface and the areas corresponding to the corner portions 23 of the cap member 20 are formed into a curved shape.

Because this shape-forming method is adopted for the sponge member 30, the areas in the sponge member 30, which corresponds to the corner portions 23 of the cap member 20, can be formed into a curved shape although configuration is simple. Additionally, because the areas in the sponge member, which correspond to the corner portions 23 of the cap member 20, are formed into a curved shape, denudation of the beauty treatment agent having been applied onto the skin surface by the cosmetic device can be effectively prevented even when the cosmetic device is slid on the skin surface. Furthermore, because of this configuration of the sponge member 30, friction generated with the skin surface can be reduced, improving the feel of the device against the skin.

Figure 5:
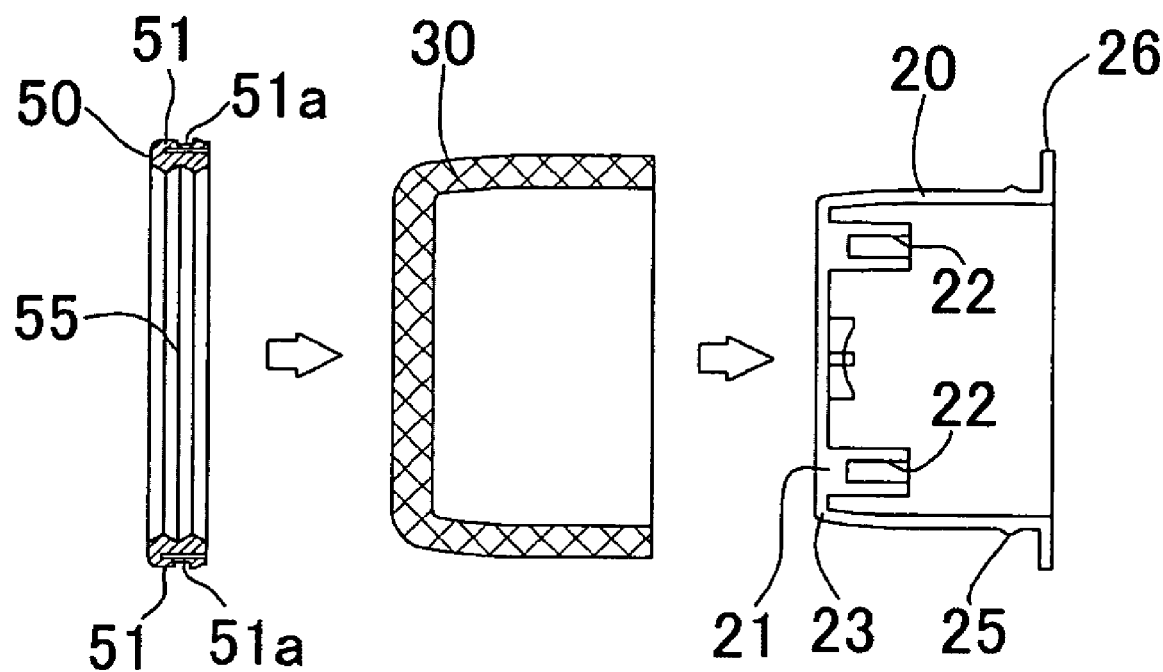
FIG. 5 is an explanatory diagram showing a state in which the sponge member 30 is fixed with the cap member 20 by the fixing member 50.
Figure 6:
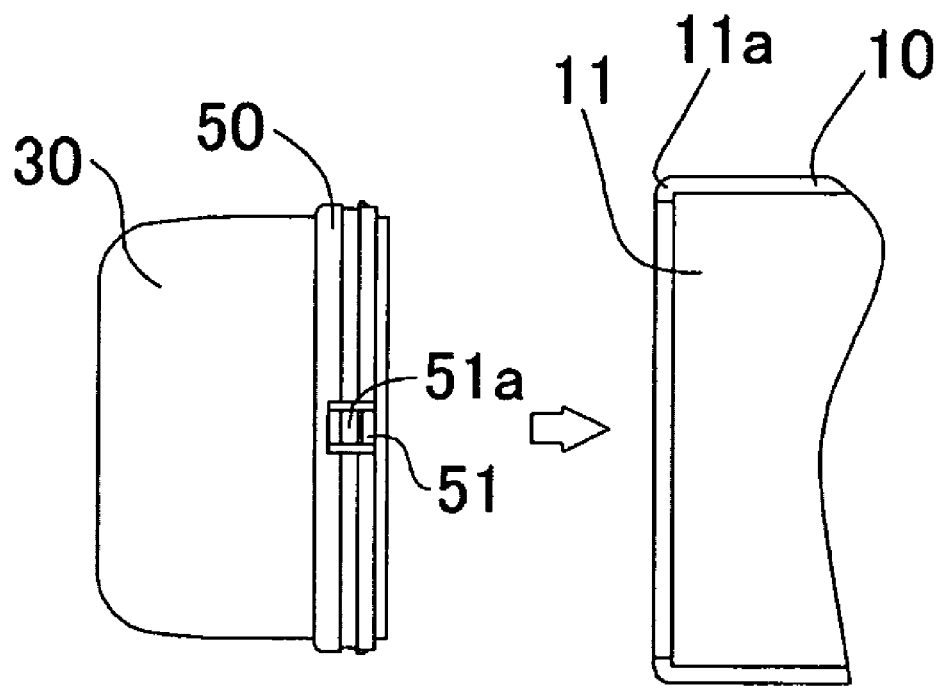
FIG. 6 is an explanatory diagram showing a state in which the cap member 20 and the sponge member 30, which are fixed by the fixing member 50, are fixed with the support member 10.

FIG. 5 is an explanatory diagram showing a state in which the sponge member 30 is foxed with the cap member 20 by the fixing member 50. FIG. 6 is an explanatory diagram showing a state in which the cap member 20 and the sponge member 30, which are fixed by the fixing member 50, are fixed with the support member 10.

The fixing member 50 has a configuration such that it fixes the sponge member 30 with the cap member 20 by holding the entire outer circumference of the sponge member 30 tightly with the cap member 20. The ends of the sponge member 30 may be placed against an annular flange 26. In this embodiment, the fixing member 50 has an inner circumference having an annular concave 55 which corresponds to an annular convex 25 formed on an outer circumference of the cap member 20, so that the sponge member 30 can be fixed between the fixing member 50 and the cap member 20 at the engaging point defined by the annular concave 55 and the annular convex 25. The sponge member 30 is resilient and deformed when interposed between the annular concave 55 and the annular convex 25, thereby being engaged with the cap member 20. When the sponge member 30 is fixed with the cap member 20 using this fixing member 50, the sponge member 30 is fitted into the cap member 20 in such a way that it covers at least the front face 21 of the cap member 20 as shown in FIG. 5. In this state, the fixing member 50 is inserted/fitted from the outside of the sponge member 30. Additionally, as shown in FIG. 6, by fitting the fixing member 50 fixing the sponge member 30 with the cap member 20 into the support member 10, the sponge member 30 and the cap member 20 are fixed with the support member 10. In an embodiment, the fixing member 50 can be integrated with the sponge member 30.

In an embodiment, multiple annular concaves 55 (e.g., two or three) and multiple annular convexes 25 (e.g., two or three) cab be used to more securely fix the sponge member to the cap member.

Figure 7A:
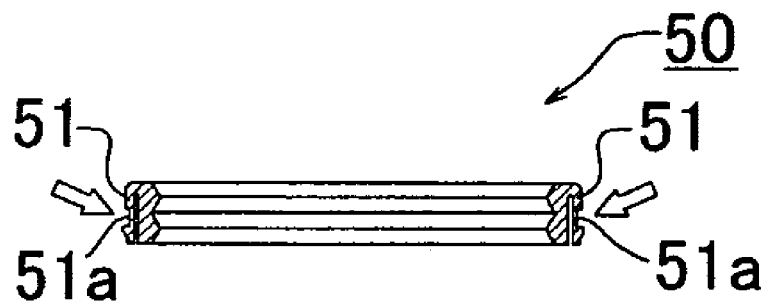
FIGS. 7(a), 7(b), and 7(c) are a cross sectional view, a side view, and an enlarged partial cross sectional view of the fixing member 50, respectively.
Figure 7B:
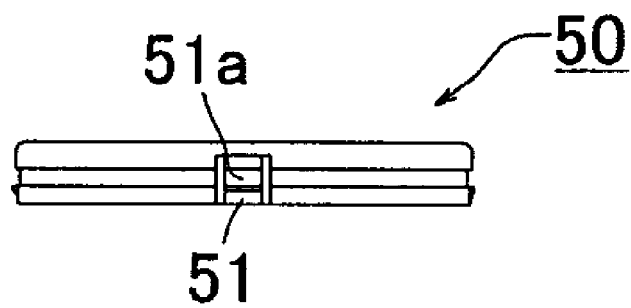
Figure 7C:
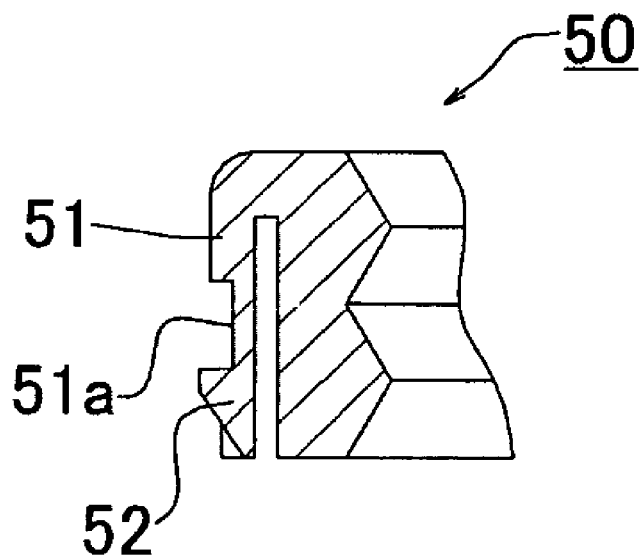

FIG. 7 is an explanatory diagram showing the fixing member 50. Of these figures, FIG. 7 (a) shows a cross section of the fixing member 50; FIG. 7 (b) shows a lateral side of the fixing member 50; FIG. 7 (c) shows an enlarged cross section of nail portions 51 of the fixing member 50.

The fixing member 50 comprises four nail portions 51 disposed at even intervals on its lateral side. The number of the nail portions can vary from one to 10 s, depending on the configuration. In respective nail portions 51, concave portions 51a are formed. These nail portions 51 have a cantilever structure; and have elastic force in an outward direction of the fixing member 50. When the fixing member 50 is secured with the support member 10, the nail portions 51 in the fixing member 50 are inserted into opening portions 11 in the support member 10 while warping them in an inward direction of the fixing member 50. By engaging the concave portion 51a of the fixing member 50 with the concave portion 11a of the support portion 10, the support member 10, the cap member 20 and the sponge member 30 can be fixed. A tip 52 of the fixing member 50 is angled so that the fixing member 50 can easily be inserted into the support portion 10.

When the fixing member 50 is removed from the support member 10, engagement of the concave portion 51a of the fixing member 50 and the convex portion 11a of the support member 50 are released while warping the nail portions 51 of the fixing member 50 in the inward direction of the fixing member 50. By taking the fixing member 50 out from the opening portion 11 of the support member 10, the fixing member 50 can be removed from the support member 10.

Because this cosmetic device comprises the fixing member 50 described above, the sponge member 30 can be washed by removing it from the cap member 20 or replaced with another sponge member when the sponge member becomes dirty. Consequently, this cosmetic device can be used in a hygienic state.

Figure 8:
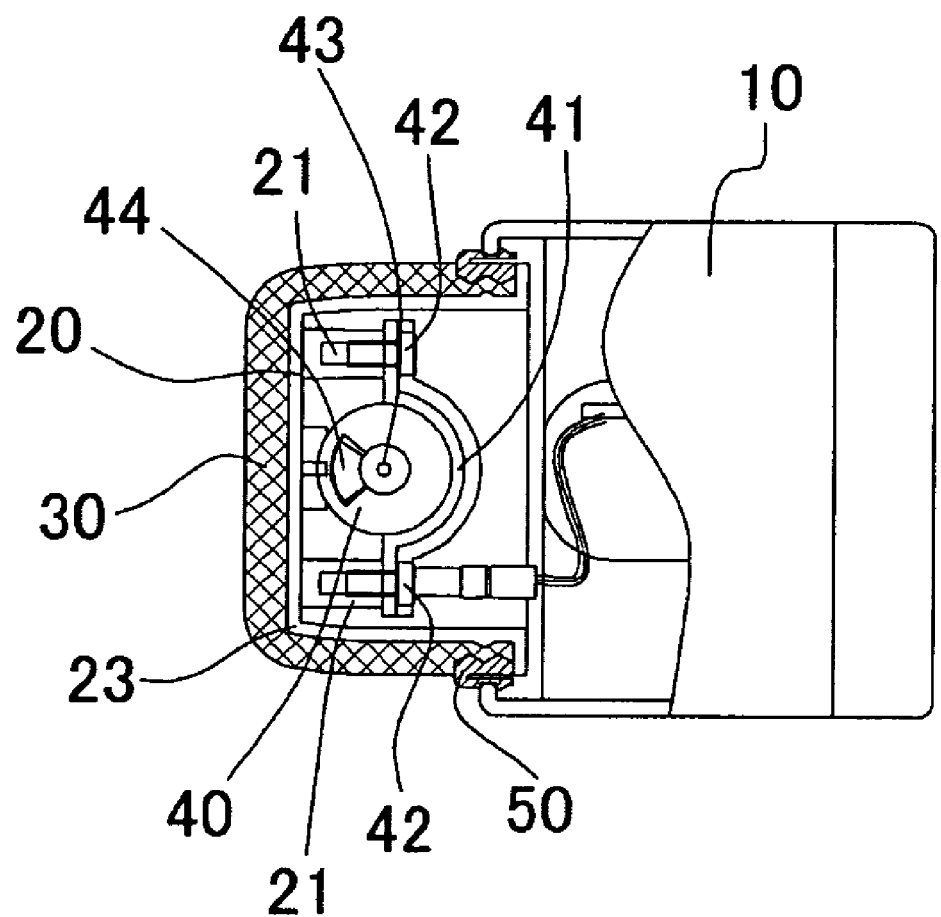
FIG. 8 is a cutaway of FIG. 1 seen from above.

FIG. 8 is a cutaway of FIG. 1 seen from above.

Referring to FIG. 2 and FIG. 8, as a vibration motor 40, for example, a vibration motor having revolutions of 8000 rpm (1000 rpm to 15000 rpm, preferably 6000 rpm to 10000 rpm) with no load and revolutions of 5700 rpm (800 rpm to 12000 rpm, preferably 4000 rpm to 8000 rpm) with appropriate load is used. This vibration motor 40 comprises a tungsten alloy eccentric weight 44 disposed at an output shaft 43 of a cylindrical continuous current motor; vibration is produced by centrifugal force difference of this eccentric weight 44 when the motor runs.

Such vibration motor 40 is disposed inside the cap member 20. Specifically, the vibration motor 40 is installed in a motor fixing member 41; by screwing a male screw 42 inserted in a hole portion 41a formed in the motor fixing portion 41 into a female screw portion 22 in the cap member 20, the vibration motor 40 is fixed with the cap member 20. By this, vibration produced by the vibration motor 40 is transmitted to the cap member 20 and the sponge member 30 fixed in the cap member 20. Consequently, by contacting a surface of the sponge member 30 of the cosmetic member with the skin surface, effective vibration can be given to the skin surface, and massage effect on the skin can be produced effectively. Particularly, because the sponge member 30 is configured to cover a surface of the cap member 20, a rounded plane angle in the skin contact surface of the cosmetic device can be provided; denudation of the beauty treatment agent having been applied onto the skin surface can be effectively prevented while processing the device is easy and at low cost.

When this type of cosmetic device is used, the sponge member 30 covering the cap member 20 is first contacted with the skin surface. In this state, the vibration motor 40 is started. By transmitting vibration produced by the vibration motor 40 to the skin via the cap member 20 and the sponge member 30, this cosmetic device is able to produce effective massage effect on the skin.

Figure 9:
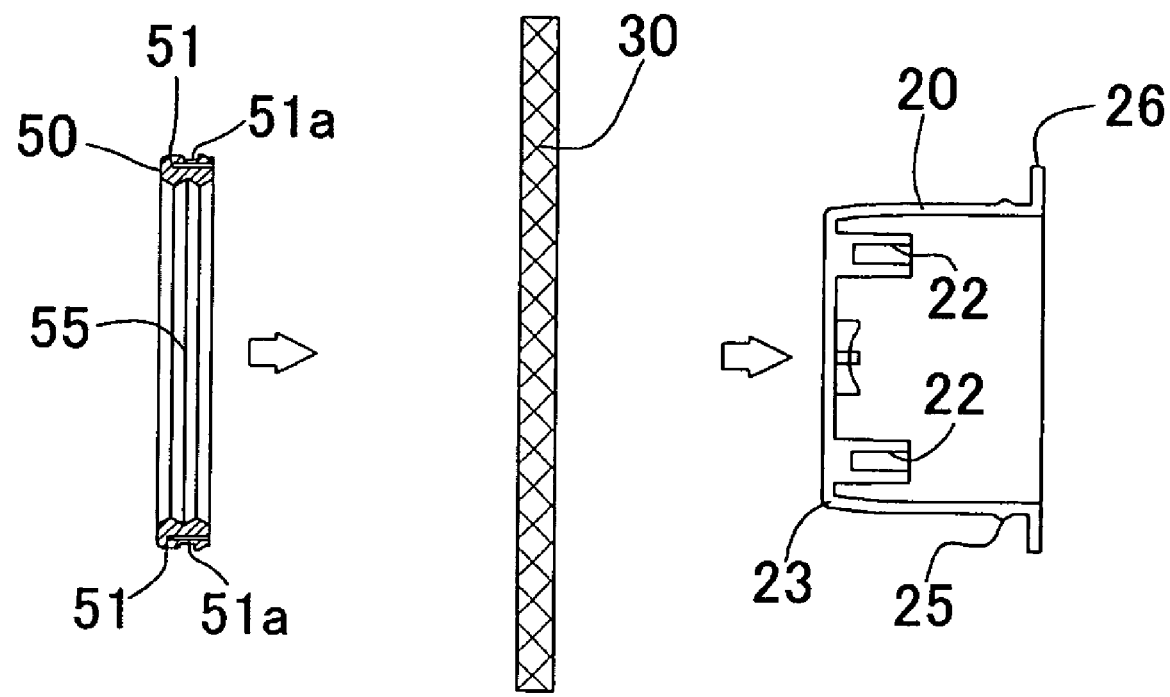
FIG. 9 is an explanatory diagram showing that the sponge member 30 is fixed with the cap member 20 by the fixing member 50 in an alternative embodiment of the present invention.

FIG. 9 is an explanatory diagram showing a state in which the sponge member 30 is fixed with the cap member 20 by the fixing member 50 according to an alternative embodiment of the present invention.

In the embodiment of the cosmetic device described above, the sponge member 30 is formed into a shape accommodating a shape of the front face 21 of the cap member 20 by press work, and the areas in the sponge member 30, which correspond to corner portions 23 of the cap member 20, are formed into a curved shape. As shown in FIG. 8, however, a planate sponge member 30 having flexibility can be used. This sponge member 30 is spread on at least the front face 21 in the cap member along its shape.

In this state, being fixed by the fixing member 50, the sponge member 30 changes its shape to the same shape as that of the sponge member 30 shown in FIG. 6. By using this planate sponge member 30 having flexibility the areas in the sponge member 30, which correspond to the corner portions 23 in the cap member 20, can also be formed into a curved shape while configuration is simple. The sponge member 30 is fixed between the fixing member 50 and the cap member 20 at the engaging point defined by the annular concave 55 and the annular convex 25.

Figure 10:
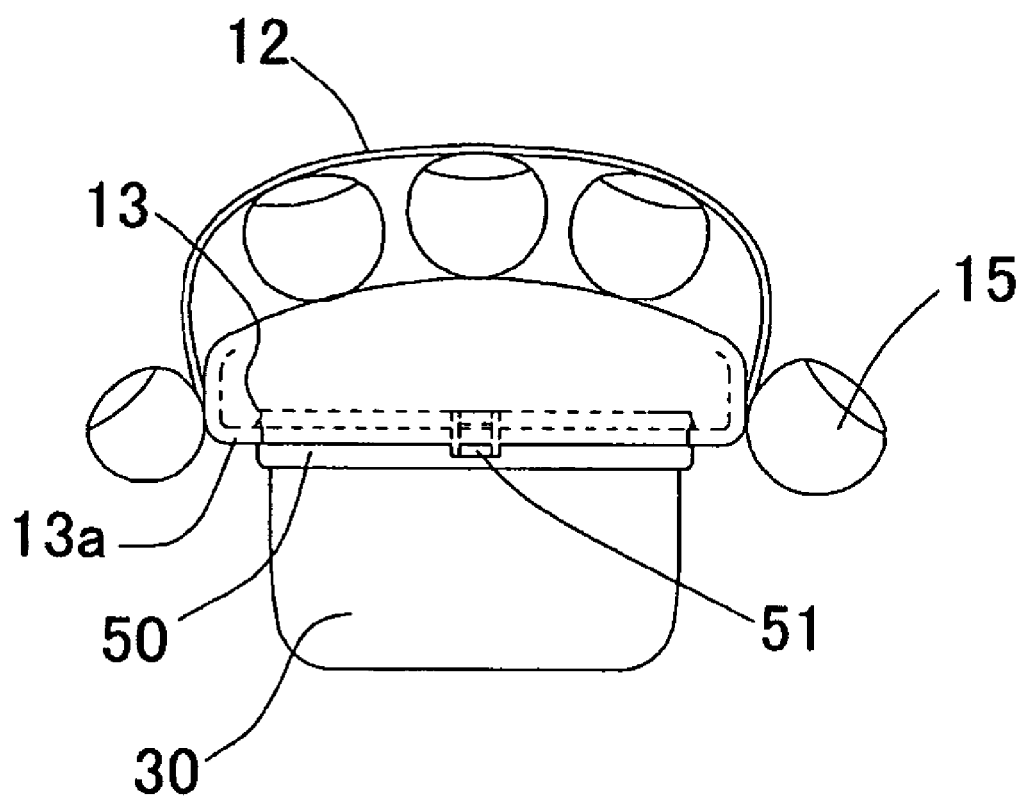
FIG. 10 is a front view showing a cosmetic device in an alternative embodiment of the present invention.

FIG. 10 is a front view showing a cosmetic device in an alternative embodiment of the present invention.

In the embodiment previously described, a support member 10 and a cap member 20 disposed in the upper portion of the support member are provided. Instead of using the support member 10 including the griper 100, a support member 12 (e.g., a strap or belt) can be employed to hold the device with fingers 15. In this support member 12, an opening portion 13 and a convex portion 13a, which are the same kind of the opening portion 11 and the convex portion 11a in the support member 10, are formed. By engaging the concave portion 51a of the fixing member 50 with the convex portion 13a of the support member 12, the support member 12, the cap member 20, and the sponge member 30 can be fixed.

Additionally, the cosmetic device without using the vibration motor 40 installed inside can be used. Without activating the vibration motor 40, by patting the skin surface with the cosmetic device or sliding it on the skin surface by holding it by hand, a beauty effect can be provided to the skin surface or a beauty treatment agent can be applied onto the skin surface.

Additionally, in the embodiment of the cosmetic device previously described, the vibration motor is used as a vibration actuator; however, an ultrasonic oscillator, etc. can also be used as a member producing vibration.

Additionally, in the embodiment of the cosmetic device previously described, the fixing member 50 comprises four nail portions 51. The number of nail portions is not limited to four; it can be any number if it is two or more.

Furthermore, in the embodiment of the cosmetic device previously described, the single vibration actuator is provided in the upper portion of the support member 10; however, multiple vibration actuators can be provided and vibration actuators having different numbers of vibrations can also be provided.

Other preferred embodiments of the present invention are described below by referring to drawings attached.

Figure 11:
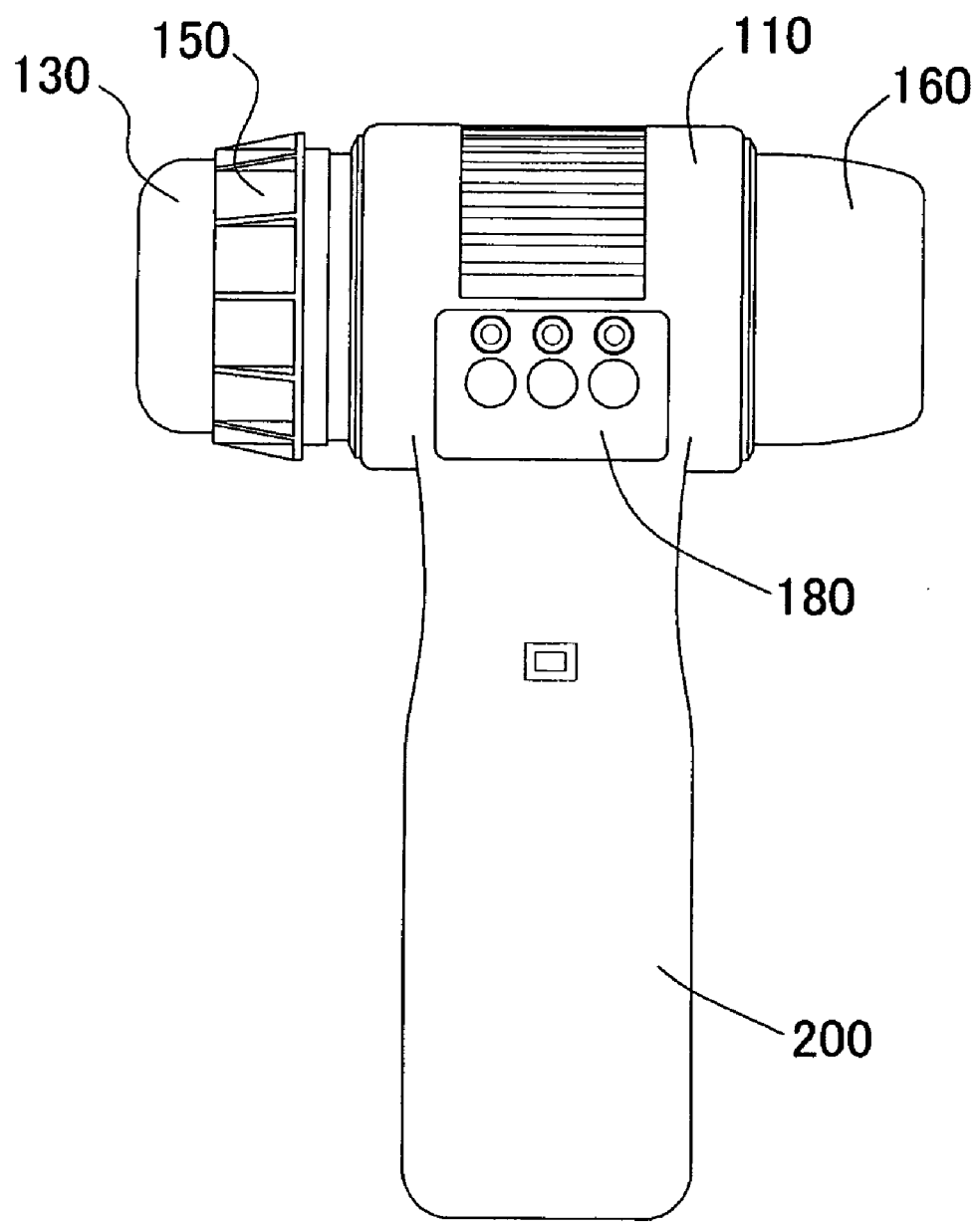
FIG. 11 is a front view showing the cosmetic device according to an embodiment of the present invention.
Figure 12:
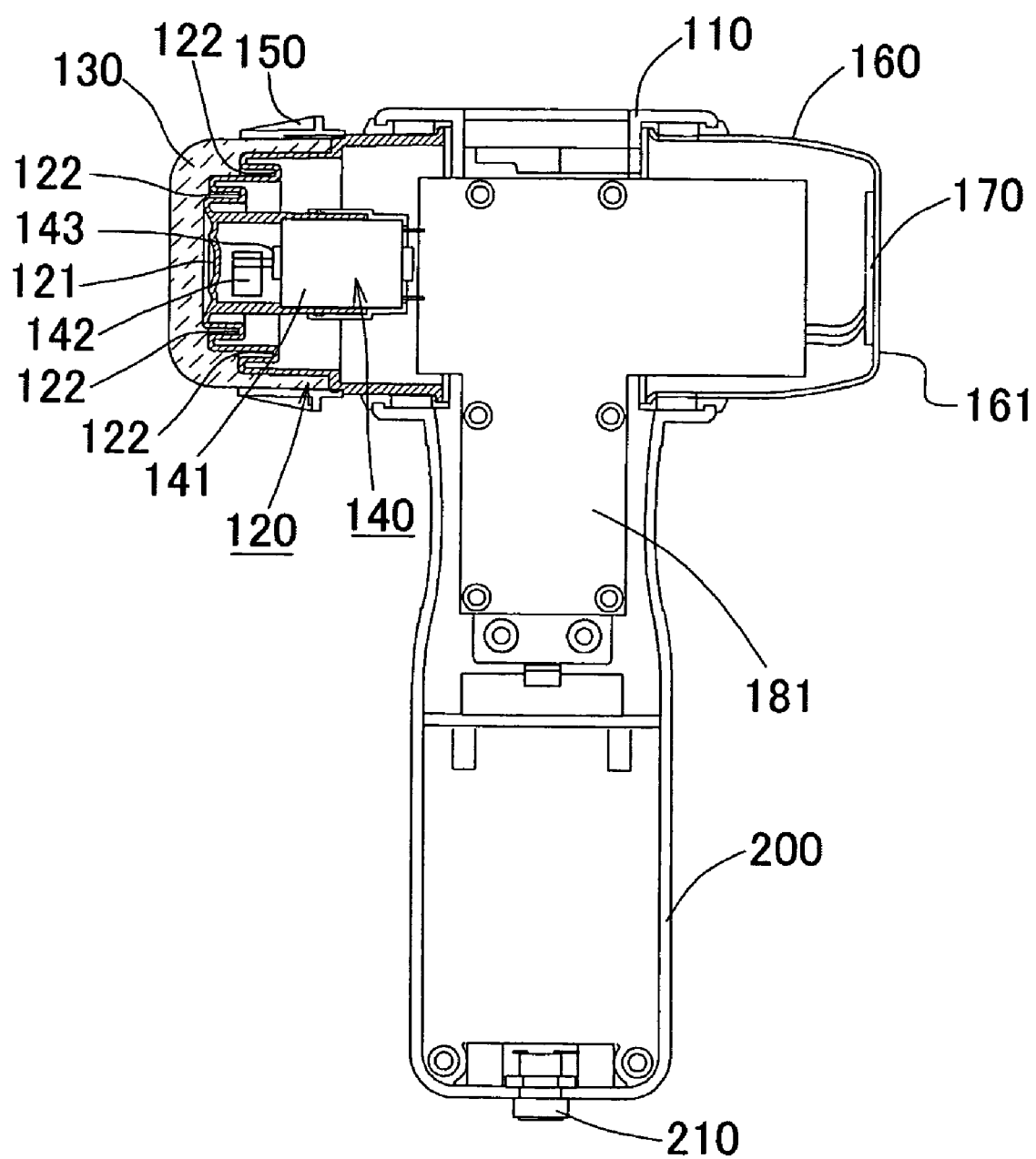
FIG. 12 is a cross section showing the cosmetic device according to an embodiment of the present invention.
Figure 13:
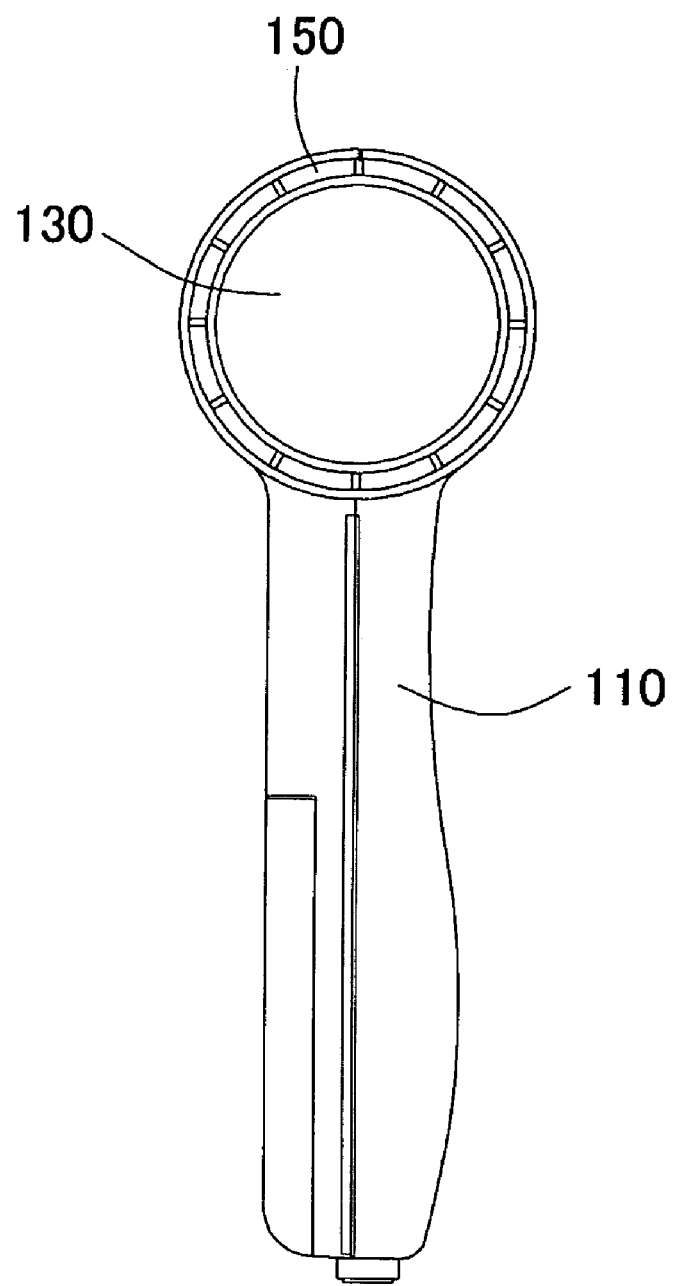
FIG. 13 is a lateral view seen from the left side of the cosmetic device according to an embodiment of the present invention.
Figure 14:
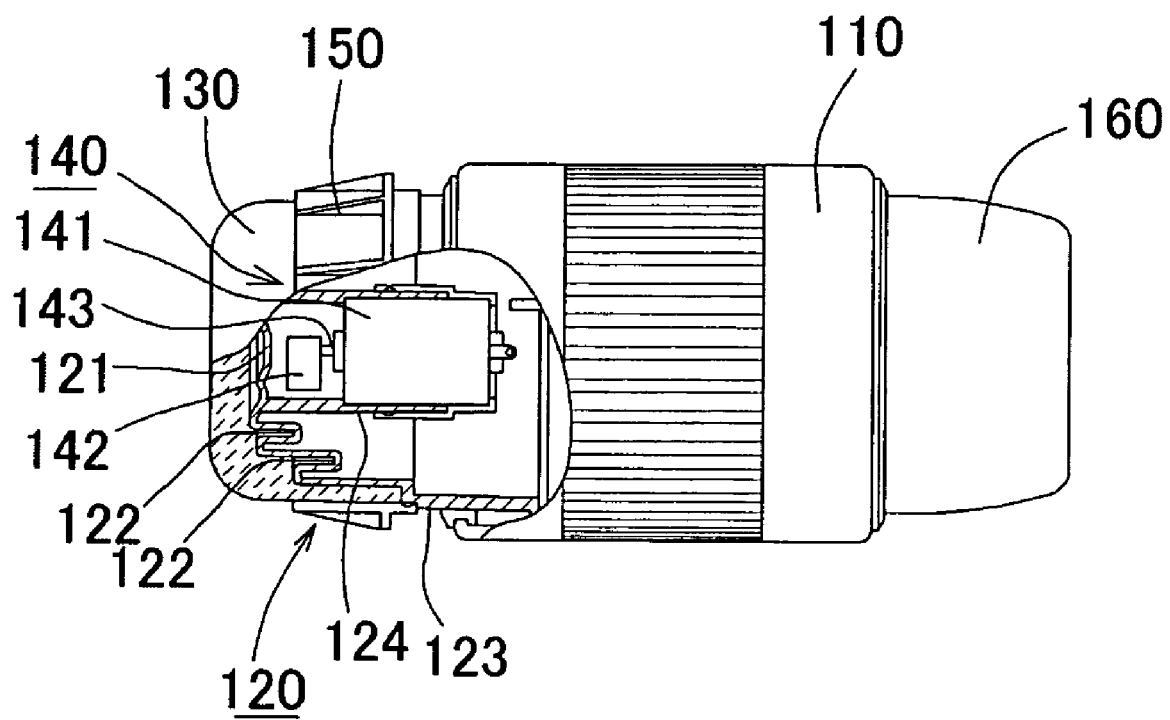
FIG. 14 is a cross section of the relevant parts of the cosmetic device according to an embodiment of the present invention shown from above.

FIG. 11 is a front view showing the cosmetic device according to an embodiment of the present invention. FIG. 12 is a cross section of FIG. 11. FIG. 13 is a lateral view of FIG. 11 seen from the left side. FIG. 14 is a plan cutaway view of a part of FIG. 11.

The cosmetic device according to an embodiment of the present invention produces a beauty effect by giving vibration to the skin. This cosmetic device comprises a support member 110, a first cap member 120 disposed in the support member 110, a vibration motor 140 as a vibration actuator, which is disposed on the inside of the first cap member 120, a second cap member 160 disposed in the support member 110, and an ultrasonic oscillator 170 disposed on the inside of the second cap member 160. The support member 110 includes a griper 200. The vibration motor 140 and the ultrasonic oscillator 170 are electrically connected with an operating panel 180 (See FIG. 11.) disposed outside the support member 110 via a distribution board 181 (See FIG. 12.).

In this embodiment, the cosmetic device comprises two heads (which can be more than two); one for physical vibration treatment, and the other for electrical vibration treatment. The electrical vibration includes, but is not limited to, ultrasonic vibration, low frequency current treatment, and/or moderate frequency current treatment. The electrical vibration treatment can be accomplished by one or more oscillator. In an embodiment, one ultrasonic oscillator provided in a conductive cap member can be used. Electric signals for ultrasonic oscillation, for example, can be provided from an external source via an electric cord through a cord connection 210 (although it can be wireless). The cord connection 210 may be an external terminal to which an external controller is connected. In this embodiment, the second cap member 160 transmits ultrasonic vibration.

In an embodiment, the vibration motor may be a motor producing vibration with an eccentric rotor provided. Vibration means is not limited to the vibration motor, and any suitable vibration-generating device can be used.

Figure 15A:
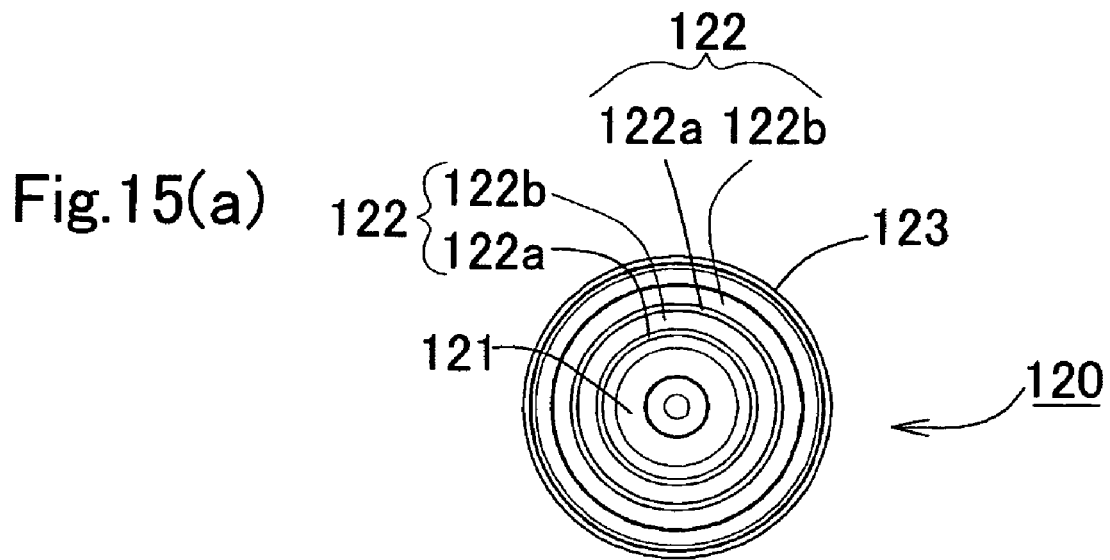
FIGS. 15(a), 15(b), and 15(c) are a top view, a side view, and a cross sectional side view of the first cap member 120, respectively.
Figure 15B:
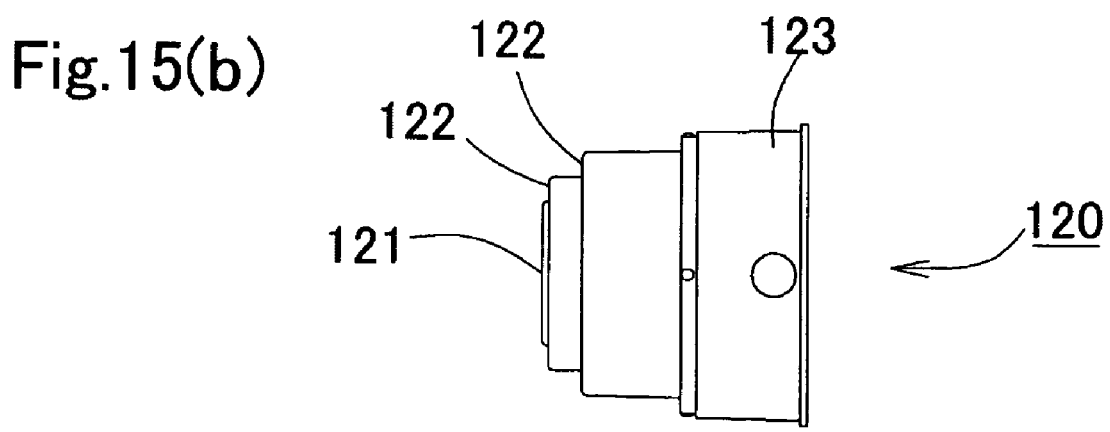
Figure 15C:
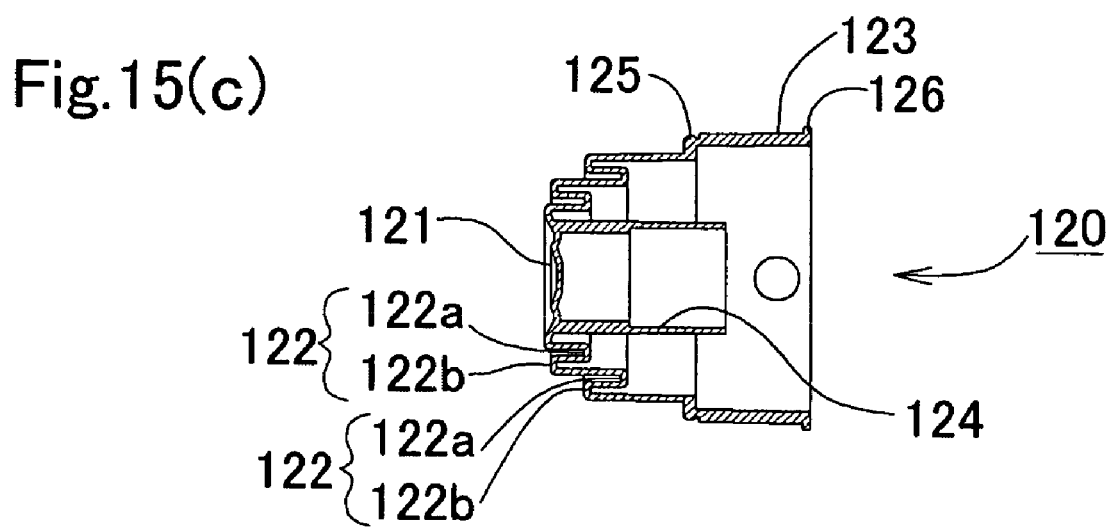
Figure 16A:
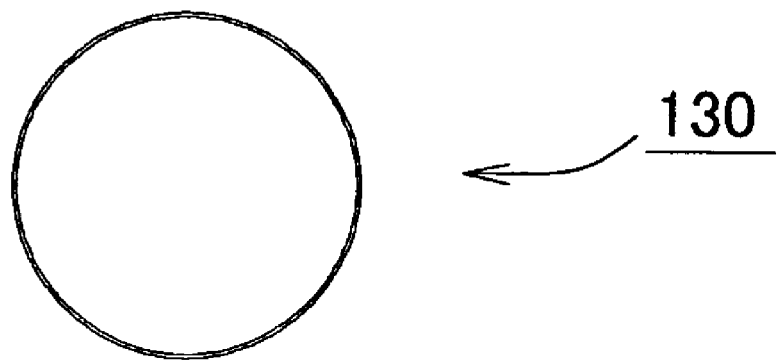
FIGS. 16(a) and 16(b) are a top view and a cross sectional side view of the sponge member 130, respectively.
Figure 16B:
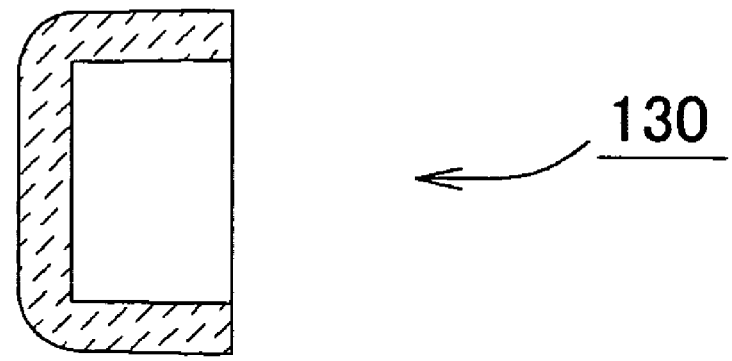
Figure 17A:
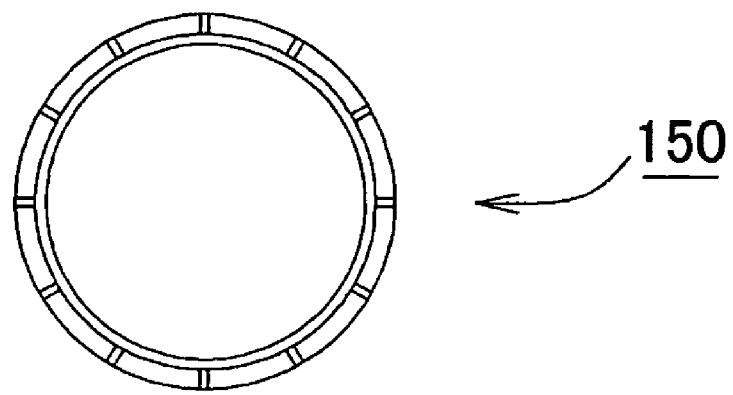
FIGS. 17(a), 17(b), and 17(c) are a top view, a side view, and a cross sectional side view of the fixing member 150, respectively.
Figure 17B:
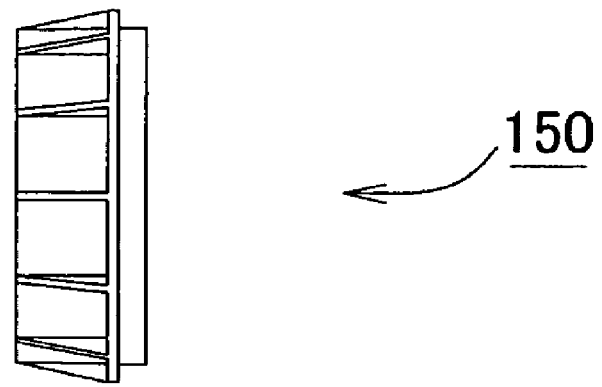
Figure 17C:
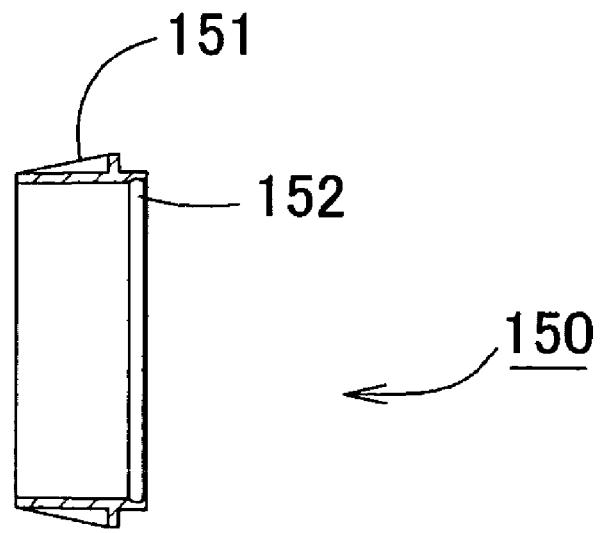

FIG. 15 is an explanatory diagram showing the fist cap member 120 comprising the cosmetic device according to an embodiment of the present invention. FIG. 16 is an explanatory diagram showing a sponge member 130 installed on an outer surface of the first cap member 120; FIG. 17 is an explanatory diagram showing the fixing member 150 for fixing the sponge member 130 with the first cap member 120. FIG. 15(a) is a front view of the first cap member 120; FIG. 15(b) is its lateral view; FIG. 15(c) is its lateral cross-section. FIG. 16(a) is a front view of the sponge member 130; FIG. 16(b) is its lateral cross-section. FIG. 17(a) is a front view of the fixing member 150; FIG. 17(b) is its lateral view; FIG. 17(c) is its lateral cross-section.

The first cap member 120 has an outer circumference portion 123 supported by the support member 110, a front face 121 positioned nearly in its center, and a double-pleat portion 122 connecting the outer circumference portion 123 and the front face 121. Additionally, on the inside of the cap member 120, a support portion 124 supporting the vibration motor 140 as a vibration actuator is formed.

The front face 121 in the first cap member 120 is formed so that it projects from a surface of the support member 110 when the outer circumference portion 123 is supported by the support member 110. Additionally, the pleat portion 122 in the first cap member 120 comprises a lower portion 122a and a higher portion 122b, which are formed annularly and nearly concentrically with the front face 121.

Additionally, on an outer circumference surface of the first cap member 120, the sponge member 130 as a porous member is installed. By fitting/inserting the fixing member 150 from outside of the sponge member 130, the first cap member 120 and the sponge member 130 are fixed. Additionally, as shown in FIG. 16, the corner portions of the sponge member 130 have a curved shape. The first cap member 120 has a flange 126 at an end connected to the supporting member 110, and an annular convex 125 at an end of the pleat portion 122. The annular convex 125 is engaged with an annular concave 152 of the fixing member 150 by interposing the sponge member 130 therebetween. The fixing member 150 has reinforcing members 151.

Consequently, denudation of a beauty treatment agent having been applied onto the skin can be prevented effectively when this cosmetic device is slid on the skin surface. Furthermore, with this configuration of the sponge member 130, it becomes possible to reduce friction generated between the cosmetic device and the skin surface.

Figure 18:
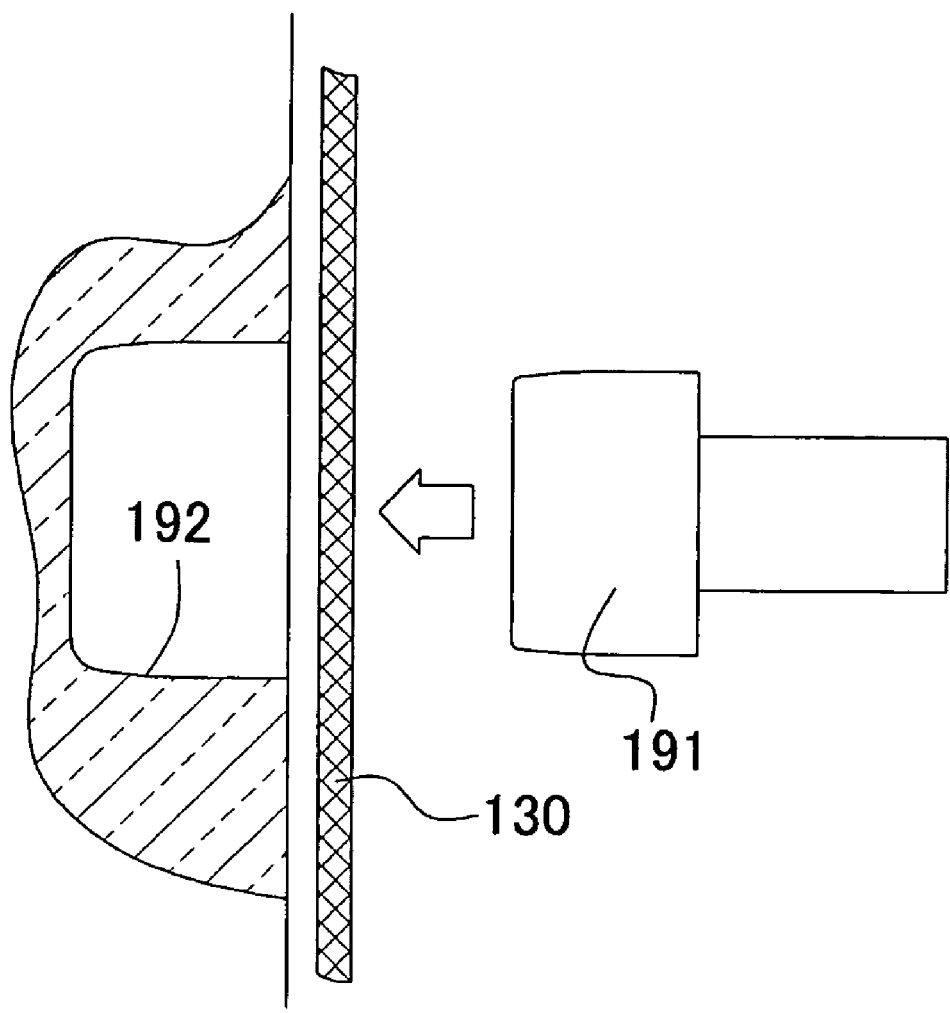
FIG. 18 is an explanatory diagram showing how the sponge member 130 is formed into a shape.

FIG. 18 is an explanatory diagram showing how the sponge member 130 is formed into a shape. The sponge member 130 can be shaped when being attached to the first cap member 120 with the fixing member 150 without being preformed.

A planate sponge member 130 is inserted between an inner mold 191 shaping a contact surface of the sponge member 130, which contacts with the first cap member 120, and an outer mold 192 shaping an outer surface of the sponge member 130; and then, the inner mold 191 moves in an arrow direction (in a direction of the outer mold 192) with pressing force sufficiently for deforming the sponge member 130. By this, the contact surface of the sponge member 130, which contacts with the first cap member 120, is deformed to the same shape as that of the inner mold 191, and the outer surface of the sponge member 130 is deformed to the same shape as that of the outer mold 192.

Additionally, as the sponge member 130, a planate sponge member having flexibility can also be used. In this case, this sponge member is spread on at least the outer surface of the front face 121 of the first cap member 120 and of the pleat portion 122 along their shapes; and then, by inserting/fitting the fixing member 150 from outside of the spread sponge member, the first cap member 120 and the sponge member 130 are fixed. In this case, because the corner portions of the sponge member 130 have a curved shape, denudation of the beauty treatment agent having been applied onto the skin can be effectively prevented when the cosmetic device is slid on the skin. Additionally, it becomes possible to reduce friction generated between the cosmetic device and the skin surface.

Figure 19:
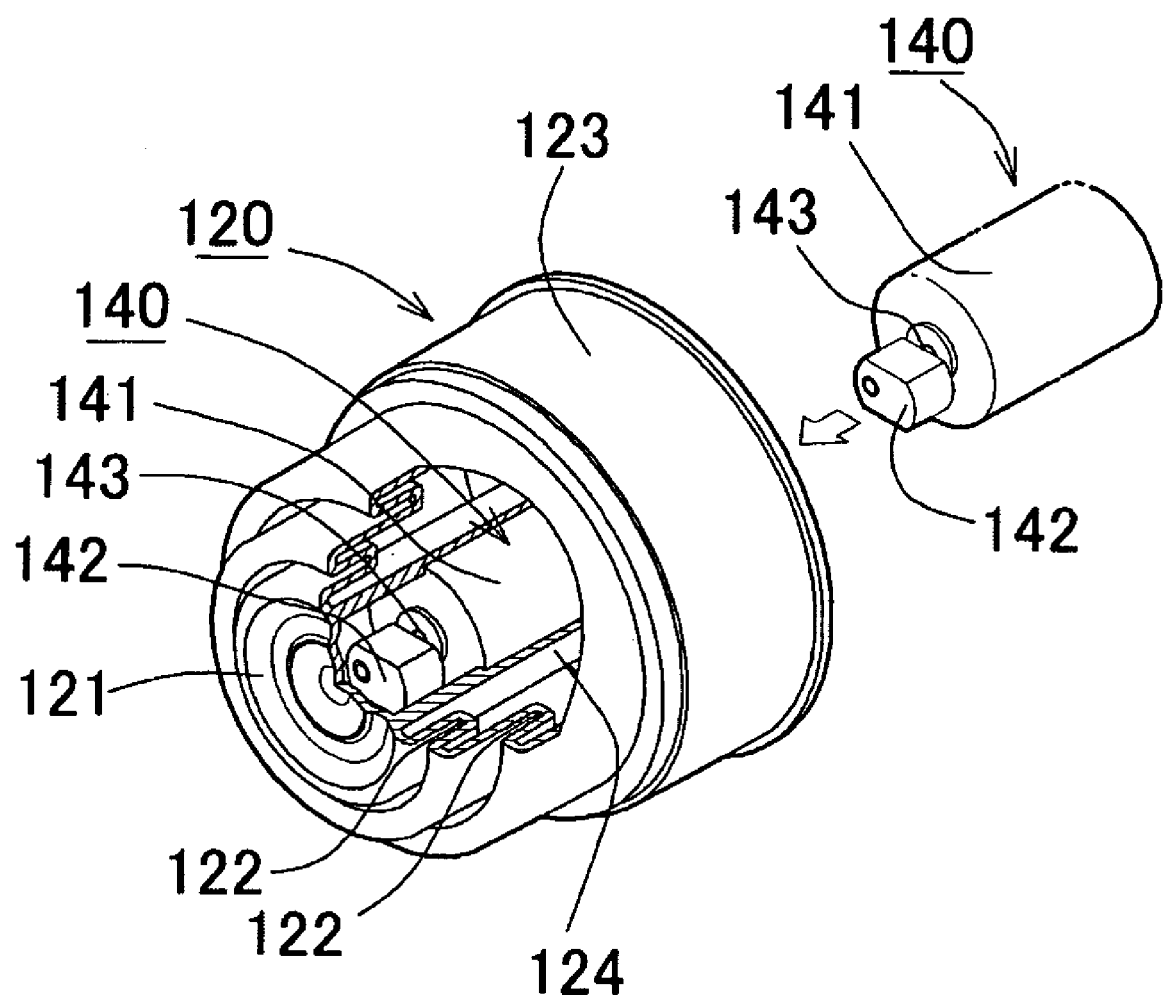
FIG. 19 is an explanatory diagram showing the first cap member 120 and the vibration motor 140.

FIG. 19 is an explanatory diagram of the first cap member 120 and the vibration motor 140.

The vibration motor 140 comprises a main unit 141, a revolving shaft 143 projecting from the main unit 141, and a weight 142 having the center of gravity in a position different from the center of the revolving shaft 143. This vibration motor 140 is supported by a support portion 124 disposed on the inside of the front face 121 in the first cap member 120. Additionally, the vibration motor 140, as shown in FIG. 12, is connected to the distribution board 181. As the revolving shaft 143 of the vibration motor 141 revolves by electrical signals supplied from the distribution panel 181, the weight 142 revolves with the revolving shaft 143 as its center. By these revolutions, the center of gravity of the vibration motor 140 is moved, causing the main unit 141 to slide. Sliding movement of the main unit 141 is transmitted to the front face 121 via the support portion 124 in the first cap member 120. Sliding movement transmitted to the front face 121 is absorbed by the pleat portion 122.

By this, vibration produced by the vibration motor 140 is not transmitted to the outer circumference portion 123 in the first cap member 120, thereby enabling to prevent the support member 110 supporting the outer circumference portion 123 from vibrating. In other words, by the pleat portion 122, it becomes possible to vibrate only the first cap member 120 and to prevent vibration of the first cam member 120 from being transmitted to other portions of the first cap member 120.

Additionally, as the vibration motor 140 used in this embodiment, a vibration motor having revolutions of 8000 rpm (1000 rpm to 15000 rpm, preferably 6000 rpm to 10000 rpm) with no load and revolutions of 5700 rpm (800 rpm to 12000 rpm, preferably 4000 rpm to 8000 rpm) with appropriate load is used. For the weight 142 of this vibration motor 140, a tungsten alloy eccentric weight is used.

Additionally, the second cap member 160 has a convex portion which projects from a surface of the support member 110 when the outer circumference portion is supported by the support member 110. This second cap member 160 is supported in a position opposing to the first cap member 120 in terms of the support member 110. Additionally, on the inside of the second cap member 160, the ultrasonic oscillator 170 (See FIG. 12.) is attached. This ultrasonic oscillator 170 is connected to the distribution panel 181 as shown in FIG. 12; and generates ultrasonic vibration by electric signals supplied from the distribution panel 181.

When this type of cosmetic device is used, the sponge member 130 is first contacted with the skin surface. In this state, by operating the operating panel 180, the vibration motor is started. By transmitting vibration produced by the vibration motor 140 to the skin via the front face 121 in the first cap member 120 and the sponge member 130, it becomes possible to produce an effective massage effect on the skin. Additionally, in this cosmetic device, in a state in which the second cap member 160 is contacted with the skin surface, by operating the ultrasonic oscillator 170 from the operating panel 180, it is possible to transmit ultrasonic vibration produced by the ultrasonic oscillator 170 to the skin via the second cap member 160 as well.

Additionally, in the embodiment previously described, the first cap member 120 has the double-pleat portion 122; however, the first cap member 120 can also have a single-pleat portion 122 or multiplex-pleat portion having two pleats or more (such as three or four).

Additionally, in the embodiment previously described, the second cap member 120 inside which the ultrasonic oscillator 170 is attached is provided; however, the second cap member 160 can be omitted.

Additionally, in the embodiment previously described, the sponge member 130 is provided as a porous member on an outer surface of the first cap member 120; however, instead of the sponge member 130, porous members having flexibility including porous resins, porous rubber, porous ceramics can also be provided.

Additionally, in the embodiment previously described, as a vibration actuator disposed on the inside of the first cap member 120, a vibration motor is used; however, a member producing other vibration can be used.

Additionally, in the embodiment previously described, a single first cap member 120 is supported by the support member 110; however, multiple first cap members can also be supported.

Figure 20:
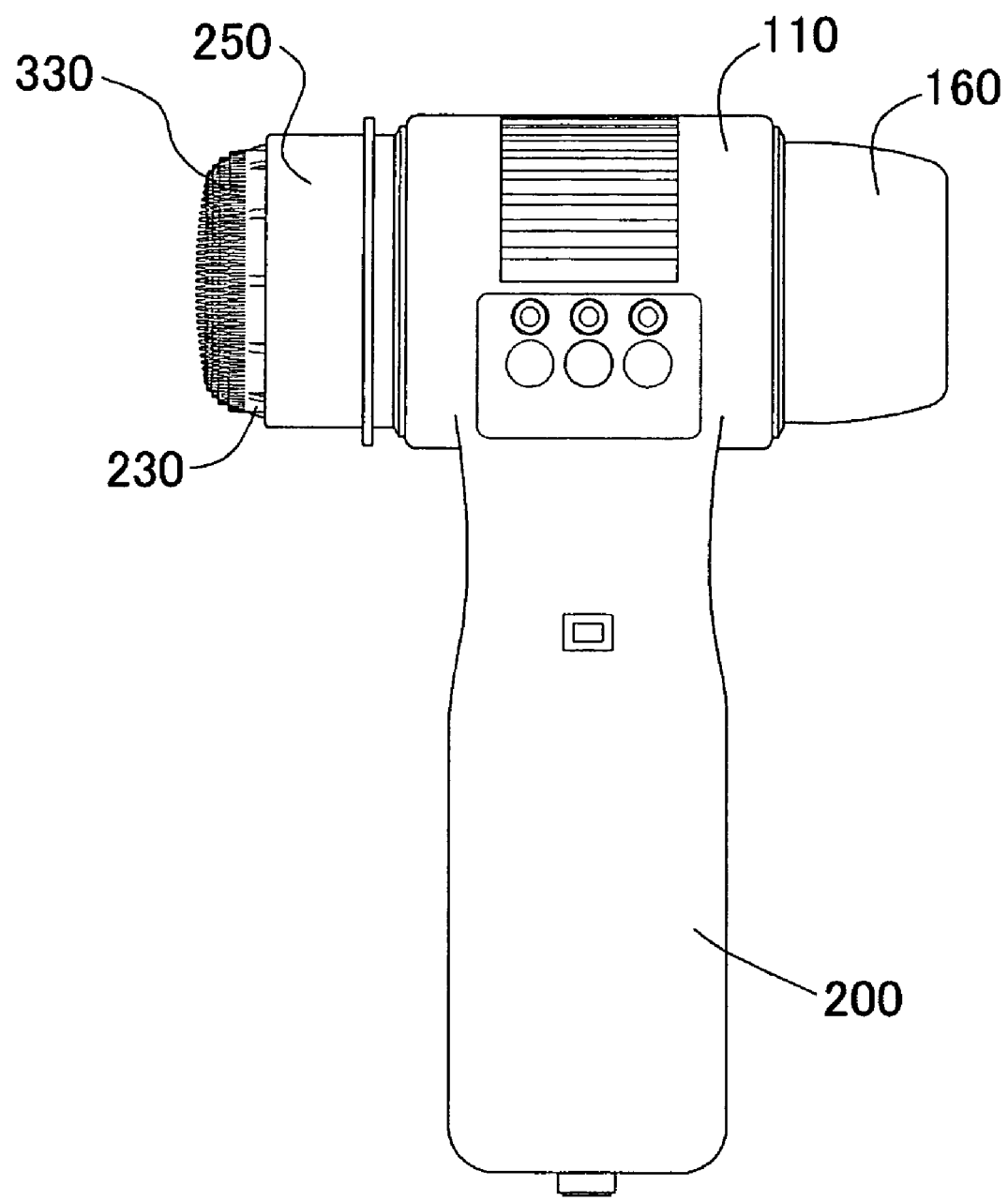
FIG. 20 is a side view of another cosmetic device according to an embodiment of the present invention.

FIG. 20 shows another embodiment of the present invention. In this embodiment, the first cap member is covered by a rough surface member 230 having multiple fine protrusions 330, instead of the sponge (or porous) member. Further, the rough surface member 230 is fixed to the support member 110 by a fixing member 250 having no reinforcing members 151. This cosmetic device has two heads and the second cap member 160 has multi functions including ultrasonic vibration, low frequency current treatment, and moderate frequency current treatment. The second cap member 160 is conductive, and thus through the second cap member, low frequency current and/or moderate frequency current can be transmitted to a skin.

Figure 21:
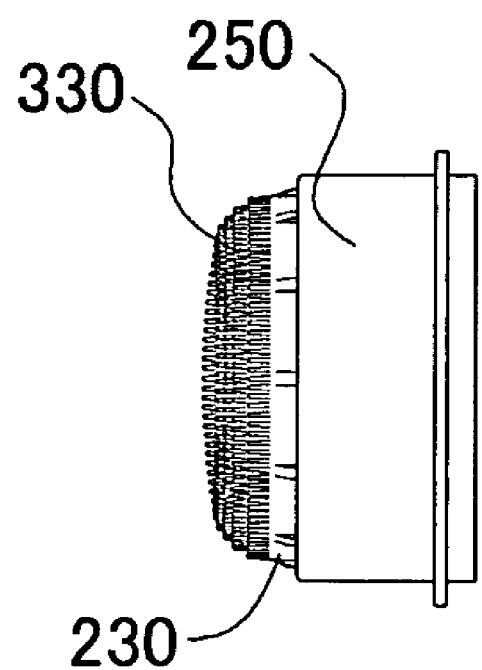
FIG. 21 is an enlarged view of multiple fine protrusions 330 and a fixing member 250.
Figure 22A:
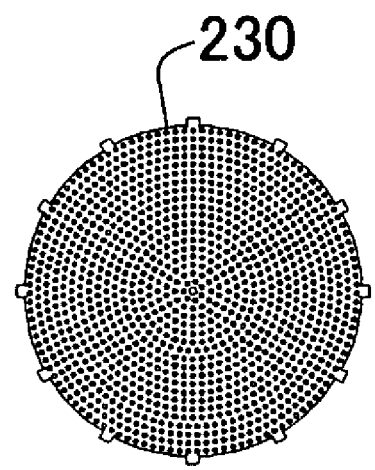
FIGS. 22(a), 22(b), and 22(c) are a top view, a side cross sectional view, and a bottom view of the uneven surface member 230, respectively.
Figure 22B:
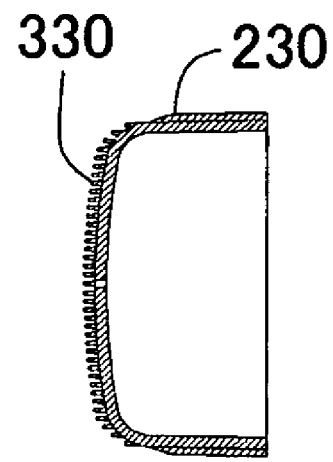
Figure 22C:
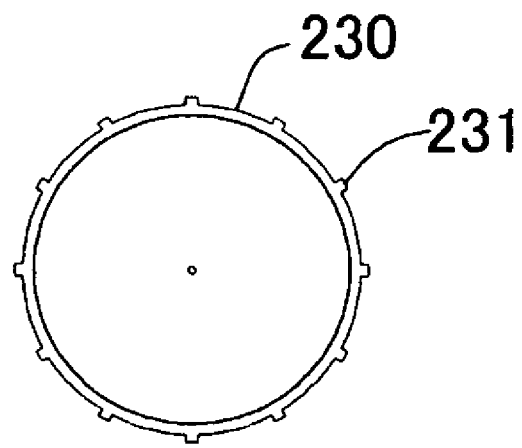

FIG. 21 is an enlarged view of the rough surface member 230 having the multiple fine protrusions 330 fixed by the fixing member 250. The rough surface member 230 can be made of the same or similar material as described in the previous embodiment; however, preferably, at least multiple fine protrusions 330 are made of a rubber based material such as silicon rubber. The number of the fine protrusions are not limited and can vary from 10 s to 100 s including, e.g., 100, 500, 1500, 3000, and ranges between any two numbers of he foregoing. The length of each protrusion may be about 1 mm to about 5 mm. The length of protrusions may be constant but can be changed in such a way that the closer the distance to the center, the longer the length becomes, or the shorter the length becomes. As shown in FIGS. 22(*a*) and 22(*b*), in this embodiment, the numerous fine protrusions 330 are formed on top of the rough surface member 230. The fine protrusions 330 may be arranged to have a curved outer surface as shown in FIG. 21. Multiple protrusions can be arranged concentrically to form a convex outer surface. Further, around the side surface, steps 231 are formed so that it becomes easy to securely fix the rough surface member 230 between the fixing member 250 and the first cap member 120 (see FIG. 22(*c*)).

Figure 23A:
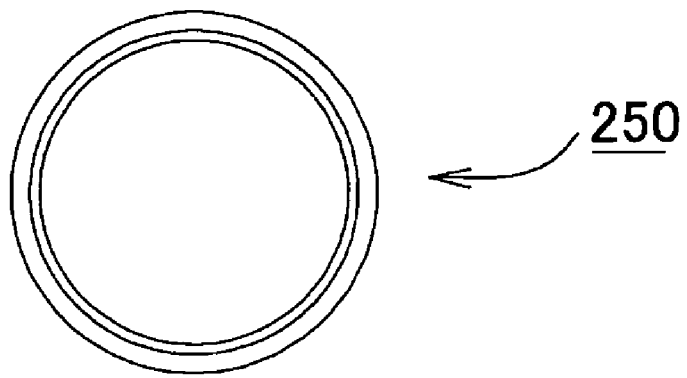
FIGS. 23(a), 23(b), and 23(c) are a top view, a side view, and a cross sectional side view of the fixing member 250, respectively.
Figure 23B:
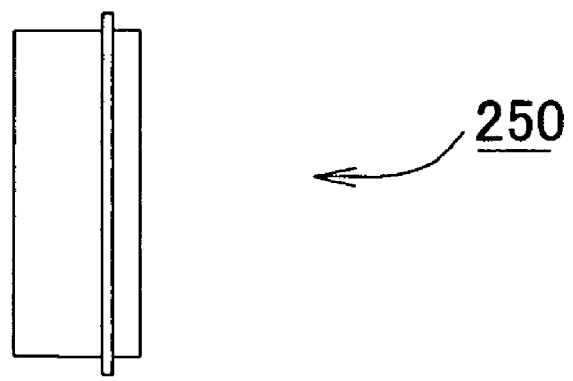
Figure 23C:
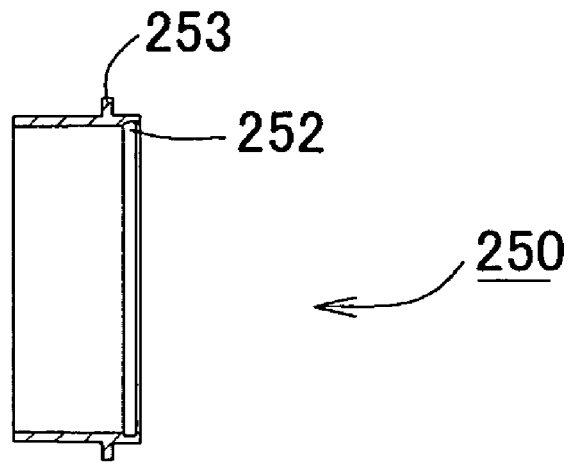

The fixing member 250 has a flange 253 so that the fixing member 250 can easily be handled as shown in FIGS. 23(*a*), 23(*b*), and 23(*c*). Further, the fixing member 250 has an annular concave 252 to fix the rough surface member 230 to the first cap member 120.

Figure 28:
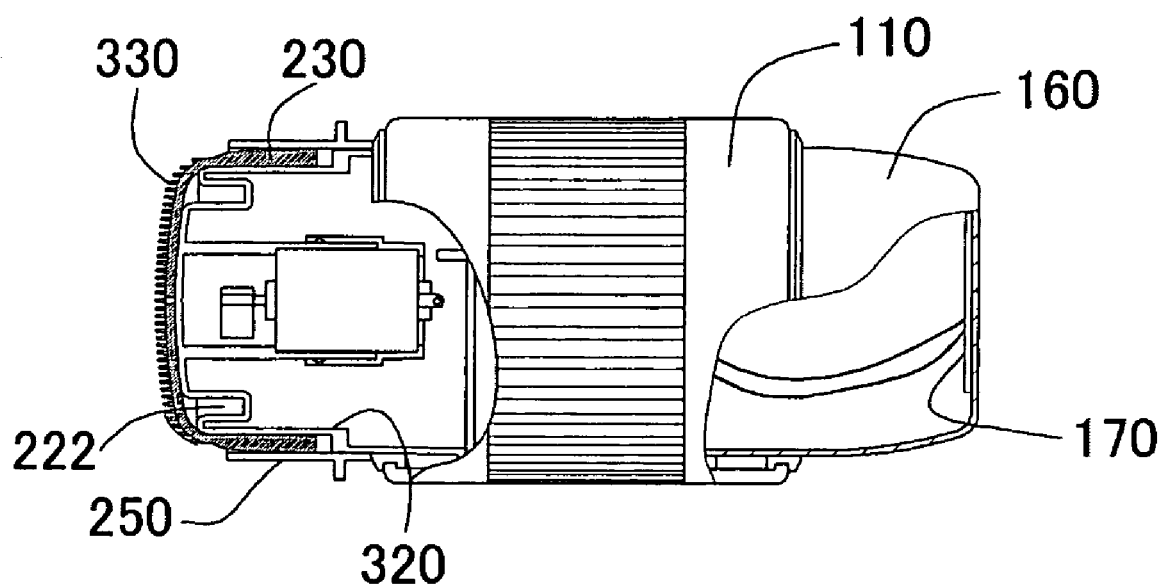
FIG. 28 is a cross section of the relevant parts of the cosmetic device according to an embodiment of the present invention shown from above.

FIG. 28 shows a cross section of relevant parts of the cosmetic device. In this embodiment, the first cap member 320 has one annular pleat portion 222. Further, the uneven surface member 230 is fixed between the fixing member 250 and the cap member 320 by press fitting, without using a convex-concave structure. In this embodiment, the fixing member 250 also does not have an annular concave as compared with that shown in FIGS. 23(*a*), 23(*b*), and 23(*c*). The fixing member 250 is fixed to the cap member 320 by press-fitting.

Figure 24:
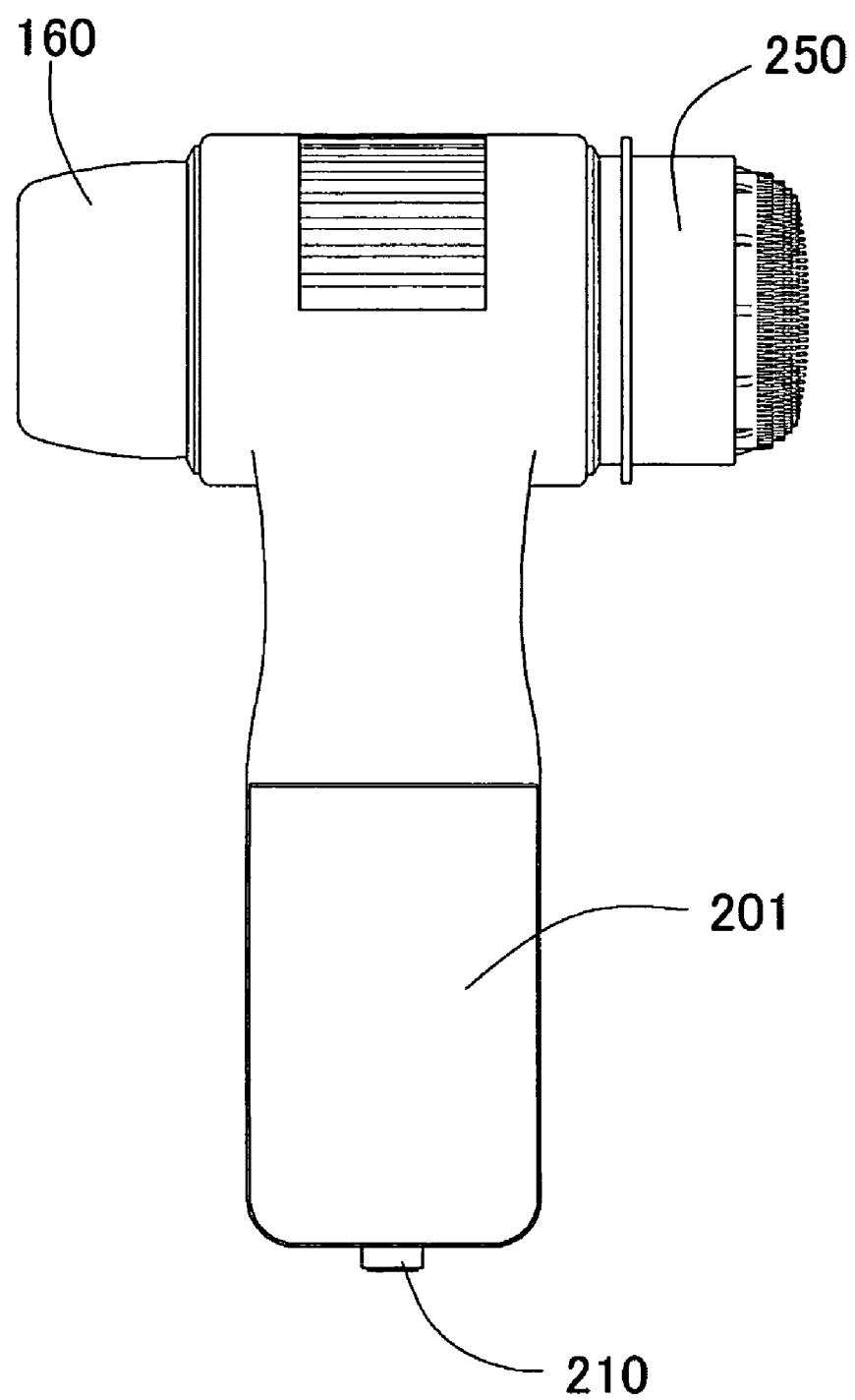
FIG. 24 is a left side view of the cosmetic device of FIG. 20.

FIG. 24 shows the reverse side of the cosmetic device. The reverse side has a slidable lid 201 in the griper 200, so that batteries can be replaced. The batteries can be a power source of the vibration motor 140. Electric signals such as ultrasonic controlling signals can be inputted into the device using the cord connection 210. Low frequency current and moderate frequency current also can be inputted into the device using the cord connection 210.

Figure 25:
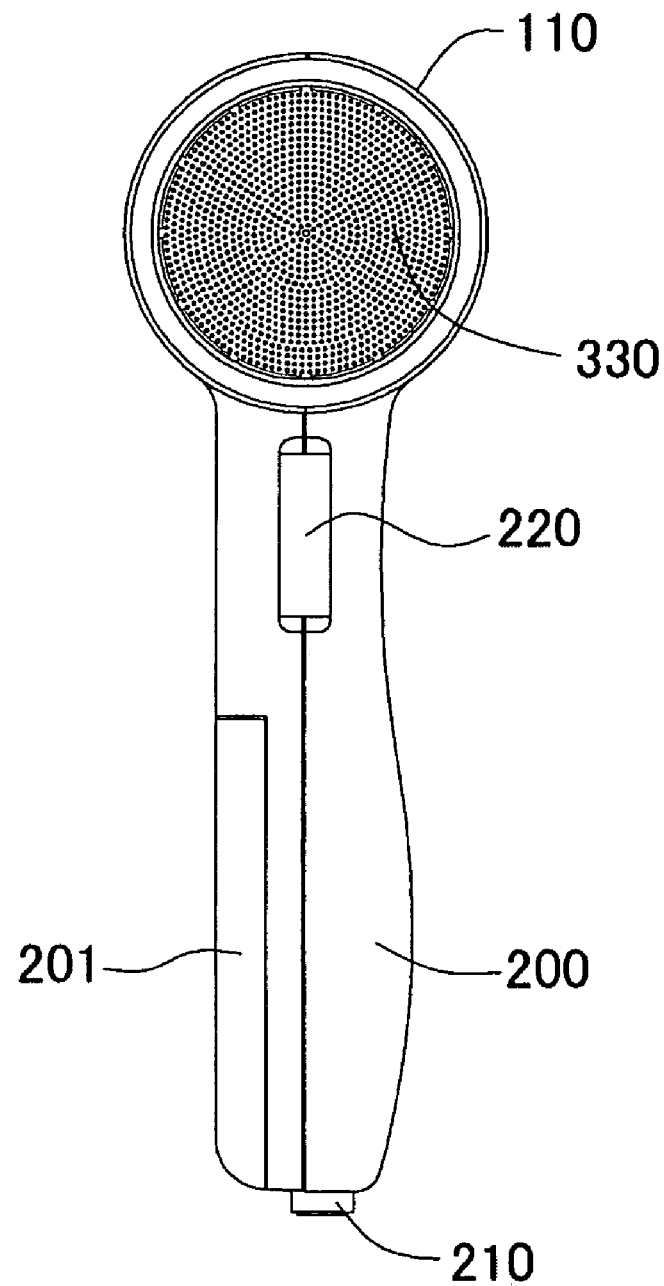
FIG. 25 is a front view of the cosmetic device of FIG. 20.
Figure 26:
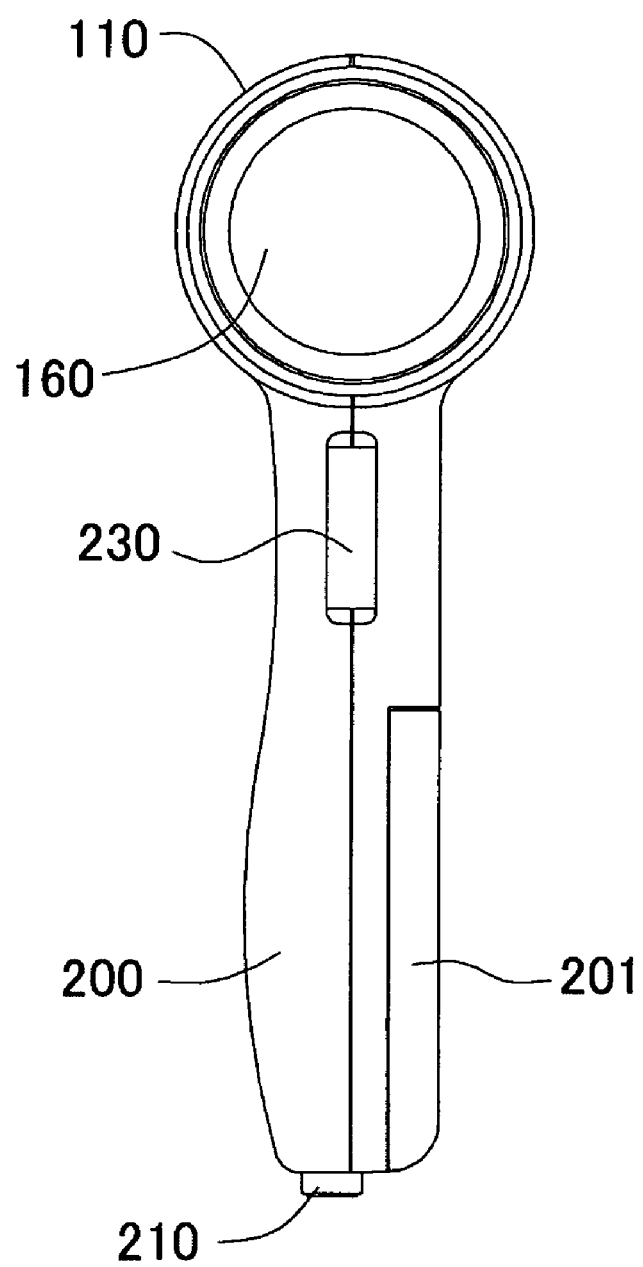
FIG. 26 is a rear view of the cosmetic device of FIG. 20.

As described above, in this embodiment, the cosmetic device is capable of treating a skin with not only physical vibration and ultrasonic oscillation, but also low frequency current and moderate frequency current. Such currents can be transmitted to the device from an external source and be exerted on a skin through the second cap member 160 which is conductive. The second cap member 160 may preferably be made of titanium or a titanium alloy which is suitable for treating a skin because it is unlikely to cause allergic reaction. In an embodiment, aluminum, aluminum alloys, other noble metals or their alloy can be used. Preferably, the second cap member 160 is produced by applying blast processing to pressed titanium, for example. When applying low frequency current and/or moderate frequency current to a skin, a user's body needs a ground terminal. FIGS. 25 and 26 show ground terminals 220 and 240. When the user holds the griper 200 of the cosmetic device, the user's hand is in contact with the ground terminals 220 and 240, so that low frequency current and/or moderate frequency current can be transmitted from the skin to the ground.

Figure 27A:
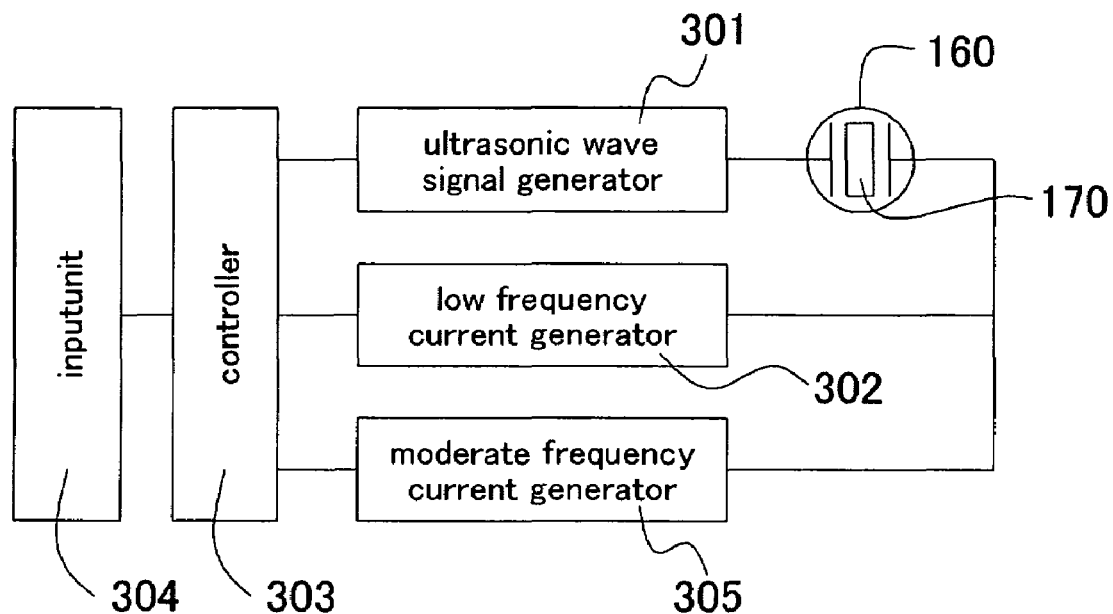
FIG. 27(a) is a wiring diagram showing main electrical configuration of the cosmetic apparatus according to an embodiment of the present invention.
Figure 27B:
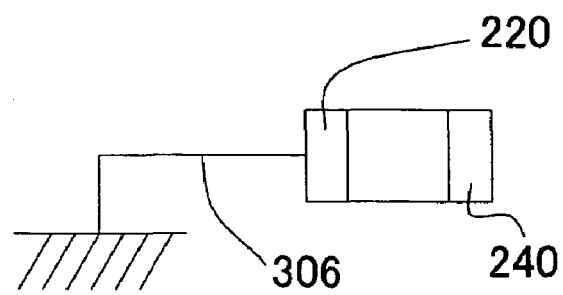
FIG. 27(b) is a schematic view of a ground separately attached to a user's hand.

FIG. 27(*a*) is a wiring diagram showing main electrical configuration of the second cap member of the cosmetic device having multiple functions. FIG. 27(*b*) shows a schematic view of ground terminals 220 and 240.

The ultrasonic oscillator 170 is provided in the second cap member 160 to which a low frequency current generator 302 and a moderate frequency current generator 305 are connected. An ultrasonic wave signal generator 301, the low frequency current generator 302 and the moderate frequency current generator 305 are connected to a controller 303 to which an input unit 304 is connected. Theses elements are installed in an external apparatus. FIG. 27(*b*) is a diagram showing the ground terminals 220 and 240 which are made of an electrically conductive material connected to the ground via a conductor 306.

In an embodiment, the second cap member 160 may be used for massaging a facial area, whereas the first cap member 120 may be used for massaging the body and/or the facial area. For the ultrasonic oscillator 170, a transducer oscillating ultrasonic vibration at a frequency of 3 MHz, which brings particularly high facial treatment effect to a facial area, may be used. For a frequency for this ultrasonic oscillator 170, a frequency at approximately 2 MHz to 4 MHz is preferable for achieving particularly high facial treatment effect to the facial area, according to an embodiment.

In another embodiment, for the ultrasonic oscillator 170, a transducer oscillating ultrasonic vibration at a frequency of 1.5 MHz, which brings particularly high slimming effect to the body, may be used. For a frequency for this ultrasonic oscillator 170, a frequency at approximately 0.5 MHz to 2 MHz is preferable for achieving high slimming effect to the body, according to an embodiment.

In this embodiment, as described above, the second cap member 160 is also used for applying low-frequency current or moderate-frequency current to the body.

The low-frequency current generating portion 302 and the moderate-frequency current generating portion 305 can be connected to the oscillator 170 which functions as low- and moderate-frequency current terminals. In an embodiment, the low- and moderate-frequency currents can be transmitted directly to the cap member 160 without passing through the ultrasonic oscillator.

In an embodiment, the cosmetic device comprises the cap members 120 and 160, whereas a control apparatus comprises the remaining elements. In another embodiment, the cosmetic device comprises the ultrasonic signal generating portion 301, the cap member 160 including the oscillator 170, and the cap member 120, whereas the control apparatus comprises the remaining elements. Any other suitable combinations can be adopted.

When massaging a facial area is given using this ultrasonic cosmetic device, 3 MHz ultrasonic vibrations are oscillated from the ultrasonic oscillator 170. This ultrasonic vibration is propagated to the second cap member 160. In this state, the second cap member 160 is brought into contact with a facial skin surface to which a gel or a cream is applied in advance. By doing so, the facial skin surface is massaged faster, and high facial treatment effect can be achieved.

For massaging the body is given using this ultrasonic cosmetic device, 1.5 MHz ultrasonic vibrations may be oscillated from the ultrasonic oscillator 170. In this state, the second cap member 160 is brought into contact with a body skin surface to which a gel or a cream is applied in advance. By doing so, the body is massaged at the frequency, which works deeply in the body, and high slimming effect can be achieved.

When a body massage is given, the low-frequency current generating portion 302 generates low-frequency current at a frequency of approximately 1 to 50 Hz, and the moderate-frequency current generating portion 305 generates moderate-frequency current at a frequency of approximately 1 to 10 KHz. These low-frequency current and moderate-frequency current are fed to the second cap member 160.

Because this cosmetic device is constructed to feed low-frequency current or moderate-frequency current to the skin through the second cap member 160 which is slid against the skin, low-frequency current or moderate-frequency current can be fed to a broad area of the skin, making it possible to achieve slimming effect in a broad area of the entire body.

Furthermore, in this cosmetic device, it becomes possible to apply low-frequency current or moderate-frequency current to the skin selectively. Consequently, a stimulus can be given to both a surface layer of the muscle layer and a deep layer of the muscle layer, making it possible to achieve slimming effect throughout the body more effectively.

Additionally, it can be constructed so that low-frequency current and/or moderate-frequency current can be fed to the second cap member 160 without the ultrasonic oscillator 170.

In the above, the "connected" includes physical direct connection, physical indirect connection, permanent connection, temporary connection, and other mechanical connection; or electrical connection, wireless connection, other functional connection, etc.

The present invention includes the above mentioned embodiments and other various embodiments including the following:

1) A cosmetic device which is characterized in that comprising a support member; a cap member disposed in said support member and having a front face projecting from a surface of said support member; a vibration actuator disposed inside said cap member, which produces vibration; and a porous member disposed in such a way that it covers a surface of the front face in said cap member.

2) The cosmetic device according to Item 1, wherein said cap member has a cylindrical shape having a bottom, and areas in said porous member, which correspond to corner portions of the cap member, have a curved shape.

3) The cosmetic device according to Item 2, wherein said porous member is removably attached to said cap member.

4) The cosmetic device according to Item 3, wherein said porous member is formed into a shape covering at least the surface of the front face in said cap member by press work.

5) The cosmetic device according to Item 3, wherein said porous member comprises a planate material having flexibility and is spread along a surface shape of the front face in said cap member.

6) The cosmetic device according to Item 4 or Item 5, wherein an annular fixing member which fixes said porous member with said cap member by holding its entire outer circumference tightly with said cap member is provided.

7) The cosmetic device according to Item 6, wherein by fitting said fixing member fixing said porous member with said cap member into said support member, said porous member and said cap member are fixed with said support member.

8) The cosmetic device according to any one of Items 1 to 7, wherein said vibration actuator comprises a vibration motor.

According to the invention described in Item 1 and Item 2, because the porous member disposed in such a way that it covers a surface of at least the front face in the cap member is provided, the invention can be processed easily and at low cost as well as denudation of the beauty treatment agent having been applied onto the skin can be effectively prevented.

According to the invention described in Item 3, because the porous member is removably attached to the cap member, the porous member can be replaced. Because of this feature, the porous member which contacts the skin surface can be maintained in a clean state.

According to the invention described in Item 4 and Item 5, although it is of simple configuration, areas in the porous member, which correspond to the corner portions of the cap member, can have a curved shape.

According to the invention described in Item 6 and Item 7, because an annular fixing member which fixes the porous member with the cap member by holding its entire outer circumference tightly with the cap member is provided, the porous member can be replaced easily.

According to the invention described in Item 8, because the vibration actuator comprises a vibration motor, effective vibration is given to the skin surface.

9) A cosmetic device which is characterized in that comprising a support member; a cap member having an outer circumference portion supported by said support member, a convex portion disposed nearly in its center and projecting from a surface of said support member, and an annular pleat portion nearly concentric with said convex portion, which connects said outer circumference portion and said convex portion; and a vibration actuator disposed on the inside of the convex portion in said cap member, which produces vibration.

10) The cosmetic device according to Item 9, wherein said cap member has multiple pleat portions.

11) The cosmetic device according to Item 9 or Item 10, wherein said vibration actuator comprises a vibration motor.

12) A cosmetic device which is characterized in that comprising a support member; a first cap member having an outer circumference portion supported by said support member, a convex portion disposed nearly in its center and projecting from a surface of said support member, and an annular pleat portion nearly concentric with said convex portion, which connects said outer circumference portion and said convex portion; a vibration actuator disposed on the inside of the convex portion in said first cap member, which produces vibration; a second cap member disposed in said support member and having a convex portion projecting from a surface of said support member; and an ultrasonic oscillator disposed on the inside of said second cap member.

13) The cosmetic device according to Item 12, wherein said first cap member has multiple pleat portions.

14) The cosmetic device according to Item 12 or Item 13, wherein said vibration actuator comprises a vibration motor.

15) The cosmetic device according to any one of Items 9 to 14, wherein on an outer surface of said first cap member, a porous member is disposed.

16) The cosmetic device according to Item 15, wherein areas in said porous member, which correspond to corner portions of said first cap member, have a curved shape.

According to the invention described in Item 9, because the annular pleat portion nearly concentric with the convex portion, which connects the outer circumference portion and the convex portion, is provided, only the limited portion in the cosmetic device can be vibrated, thereby enabling to prevent vibration produced by the vibration actuator from being transmitted to the support member.

According to the invention described in Item 10, because the cap member has multiple pleat portions, assuredly only the limited portion in the cosmetic device can be vibrated, thereby enabling to prevent vibration produced by the vibration actuator from being transmitted to the support member.

According to the invention described in Item 11, because the vibration actuator disposed on the inside of the cap member comprises a vibration motor, appropriate vibration can be given to the skin, thereby enabling to prevent vibration produced by the vibration actuator from being transmitted to the support member.

According to the invention described in Item 12, because the annular pleat portion nearly concentric with the convex portion, which connects the outer circumference portion and the convex portion, is provided, only the limited portion in the cosmetic device can be vibrated, thereby enabling to prevent vibration produced by the vibration actuator from being transmitted to the support member; and hence enabling to prevent vibration produced by the vibration actuator disposed on the inside of the first cap member from affecting the ultrasonic oscillator connected with the same support member.

According to the invention described in Item 13, because the first cap member has multiple pleat portions, assuredly only the limited portion in the cosmetic device can be vibrated, thereby enabling to prevent vibration produced by the vibration actuator from being transmitted to the support member.

According to the invention described in Item 14, because the vibration actuator disposed on the inside of the first cap member comprises a vibration motor, appropriate vibration is given to the skin, thereby enabling to prevent vibration produced by the vibration actuator from being transmitted to the support member.

According to the invention described in Item 15, because the porous member is disposed on the outer surface of the first cap member, denudation of the beauty treatment agent having been applied onto the skin can be prevented effectively while processing the device is easy and at low cost, and it becomes possible to transmit vibration produced by the vibration actuator to the skin effectively.

According to the invention described in Item 16, because the areas in the porous member, which correspond to the corner portions of the first cap member, have a curved shape, denudation of the beauty treatment agent having been applied onto the skin can be prevented effectively while processing the device is easy and at low cost.

The present application claims priority to Japanese Patent Application No. 2003-364672, filed Oct. 24, 2003, and No. 2004-147881, filed May 18, 2004, the disclosure of which is incorporated herein by reference in their entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A cosmetic device comprising:
a support member;
a cap member attached to the support member and having a front face;
a vibration actuator disposed inside the cap member, which produces vibration for providing massage effect on a skin; and
an uneven surface member as an outermost layer covering at least the front face of the cap member, said uneven surface being configured to prevent denudation of a treatment agent applied on the skin,
wherein the front face of the cap member comprises at least one annular pleat structure substantially or nearly concentric with an outer circumference.

2. The cosmetic device according to claim 1, wherein the uneven surface member is a porous member.

3. The cosmetic device according to claim 2, wherein the porous member is a resilient sponge material.

4. The cosmetic device according to claim 1, wherein the uneven surface member is replaceable.

5. The cosmetic device according to claim 1, further comprising a ring member for fixing the uneven surface member wherein the uneven surface member is fixed between the ring member and the cap member.

6. The cosmetic device according to claim 5, wherein the ring member has an inner circumference having an annular concave, and the cap member has an outer circumference having an annular convex, wherein the uneven surface member is fixed between the annular concave of the ring member and the annular convex of the cap member.

7. The cosmetic device according to claim 5, wherein the uneven surface member is made of a planate material having flexibility and is shaped when is fixed to the cap member with the ring member.

8. The cosmetic device according to claim 1, wherein the cap member has an annular flange which is engaged with the support member.

9. The cosmetic device according to claim 1, wherein the cap member has an inner surface provided with a supporting structure to which the vibration actuator is supported.

10. The cosmetic device according to claim 1, wherein the front face of the cap member has a rounded annular edge.

11. The cosmetic device according to claim 1, wherein the uneven surface member is preformed in a shape corresponding to a shape of the cap member.

12. The cosmetic device according to claim 1, wherein the support member has a gripper.

13. The cosmetic device according to claim 1, wherein the vibration actuator is battery-operated.

14. The cosmetic device according to claim 13, wherein the support member is configured to accommodate a battery or batteries.

15. The cosmetic device according to claim 1, wherein the at least one annular pleat structure is constituted by multiple pleat portions.

16. The cosmetic device according to claim 1, wherein the vibration actuator is provided substantially or nearly in a center of the front face of the cap member.

17. The cosmetic device according to claim 1, wherein the uneven surface member is constituted by multiple fine protrusions.

18. The cosmetic device according to claim 17, wherein the front face of the uneven surface member is curved in a partial sphere.

19. The cosmetic device according to claim 17, wherein the multiple fine protrusions are formed in circles concentric with each other.

20. A cosmetic device comprising:
a support member;
a cap member attached to the support member and having a front face;
a vibration actuator disposed inside the cap member, which produces vibration for providing massage effect on a skin;
an uneven surface member as an outermost layer covering at least the front face of the cap member, said uneven surface being configured to prevent denudation of a treatment agent applied on the skin; and
a conductive cap member attached to the support member, said conductive cap member having a front face, wherein an ultrasonic oscillator is attached to an inner wall of the front face.

21. The cosmetic device according to claim 20, wherein the support member is configured to be connected to an external ultrasonic signal generator.

22. The cosmetic device according to claim 20, wherein the conductive cap member is electrically connected to an external low frequency current generator and/or an external moderate frequency current generator.

23. The cosmetic device according to claim 22, wherein the support member is provided with a ground terminal which is in contact with a user's hand when in use.

24. The cosmetic device according to claim 20, wherein the uneven surface member is replaceable.

25. The cosmetic device according to claim 20, wherein the vibration actuator is battery-operated.

26. A cosmetic device comprising:
a support member;
a cap member attached to the support member and having a front face;
a vibration actuator disposed inside the cap member, which produces vibration for providing massage effect on a skin;
a replaceable uneven surface member as an outermost layer covering at least the front face of the cap member, said uneven surface being such that denudation of a treatment agent applied on the skin is inhibited; and
a ring member to fix the uneven surface member wherein the uneven surface member is fixed between the ring member and the cap member,
wherein the front face of the cap member comprises at least one annular pleat structure substantially or nearly concentric with an outer circumference.

27. The cosmetic device according to claim 26, wherein the uneven surface member is constituted by a porous member or multiple fine protrusions.

28. A cosmetic device comprising:
a support member;
a first cap member attached to the support member and having a front face;
a vibration actuator disposed inside the cap member, which produces vibration for providing massage effect on a skin;
an uneven surface member as an outermost layer covering at least the front face of the cap member, said uneven surface being such that denudation of a treatment agent applied on the skin is inhibited; and
a second cap member attached to the support member, wherein an ultrasonic oscillator is provided inside the second cap member.

29. The cosmetic device according to claim 28, wherein the uneven surface member is constituted by a porous member or multiple fine protrusions.

30. The cosmetic device according to claim 28, wherein the front face of the first cap member comprises at least one annular pleat structure substantially or nearly concentric with an outer circumference.

31. The cosmetic device according to claim 28, wherein the second cap member is made of titanium or a titanium alloy.

32. The cosmetic device according to claim 28, wherein the second cap member is connected to an external low frequency current generator and/or an external moderate frequency current generator.

* * * * *